United States Patent
Hatanaka et al.

(10) Patent No.: US 12,023,636 B2
(45) Date of Patent: Jul. 2, 2024

(54) METHOD AND DEVICE FOR PRODUCING LIQUID CULTURE MEDIUM COMPOSITION

(71) Applicant: NISSAN CHEMICAL CORPORATION, Tokyo (JP)

(72) Inventors: Daisuke Hatanaka, Funabashi (JP); Hisato Hayashi, Funabashi (JP); Shinsuke Tadokoro, Funabashi (JP); Masami Kozawa, Funabashi (JP); Keisuke Morodome, Funabashi (JP)

(73) Assignee: Nissan Chemical Corporation, Tokyo (JP)

( * ) Notice: Subject to any disclaimer, the term of this patent is extended or adjusted under 35 U.S.C. 154(b) by 630 days.

(21) Appl. No.: 16/319,815

(22) PCT Filed: Jul. 21, 2017

(86) PCT No.: PCT/JP2017/026454
§ 371 (c)(1),
(2) Date: Jan. 22, 2019

(87) PCT Pub. No.: WO2018/016622
PCT Pub. Date: Jan. 25, 2018

(65) Prior Publication Data
US 2019/0262785 A1 Aug. 29, 2019

(30) Foreign Application Priority Data
Jul. 22, 2016 (JP) .................. 2016-144953

(51) Int. Cl.
*B01F 23/45* (2022.01)
*B01F 23/451* (2022.01)
(Continued)

(52) U.S. Cl.
CPC .......... *B01F 23/453* (2022.01); *B01F 23/451* (2022.01); *B01F 25/23* (2022.01);
(Continued)

(58) Field of Classification Search
CPC .... B01F 3/0873; B01F 5/0256; B01F 5/0451; B01F 3/0865; B01F 2005/0034;
(Continued)

(56) References Cited

U.S. PATENT DOCUMENTS 5,827,707 A * 10/1998 Lamberti ............. A61K 9/1652
435/178
8,658,418 B2 * 2/2014 Daridon ................. C12M 21/06
435/288.5
(Continued)

FOREIGN PATENT DOCUMENTS

CN 105567627 A 5/2016
EP 1634640 A2 3/2006
(Continued)

OTHER PUBLICATIONS

Japanese Patent Office, International Search Report in International Patent Application No. PCT/JP2017/026454 (dated Oct. 17, 2017).
(Continued)

*Primary Examiner* — Sean C. Barron
(74) *Attorney, Agent, or Firm* — Leydig, Voit & Mayer, Ltd.

(57) ABSTRACT

Provided is a method for producing a liquid medium composition, including using a junction conduit structure 10 having a structure in which a first inlet conduit 11 and a second inlet conduit 12 are joined together to form an outlet conduit 13, and flowing a first liquid 1 containing a particular compound into the first inflow conduit 11 and flowing a second liquid 2 containing a linking substance into the second inlet conduit 12, and allowing the flows of the both liquids to join together to mix the both liquids, thus forming a liquid medium composition 3 containing structures formed
(Continued)

by the particular compound linked via the linking substance dispersed therein while being flown through the outlet conduit 13.

4 Claims, 8 Drawing Sheets

(51) Int. Cl.
    *B01F 25/00*     (2022.01)
    *B01F 25/23*     (2022.01)
    *B01F 25/313*     (2022.01)
    *C12M 1/00*     (2006.01)
    *C12N 5/00*     (2006.01)

(52) U.S. Cl.
    CPC ........ *B01F 25/313* (2022.01); *B01F 25/3131* (2022.01); *C12M 99/00* (2013.01); *C12N 5/0018* (2013.01); *B01F 2025/918* (2022.01); *B01F 2025/91911* (2022.01); *C12N 2500/14* (2013.01); *C12N 2500/16* (2013.01); *C12N 2500/50* (2013.01)

(58) Field of Classification Search
    CPC .............. C12N 5/0018; C12N 2500/50; C12N 2500/14; C12N 2500/16
    See application file for complete search history.

(56) References Cited

U.S. PATENT DOCUMENTS

2006/0056271 A1* 3/2006 Kapila ................. B01F 5/0256
    366/181.5
2007/0227971 A1* 10/2007 Denney ..................... C02F 1/56
    210/606
2009/0269250 A1 10/2009 Panagiotou et al.
2011/0137012 A1 6/2011 Katayama et al.
2014/0106348 A1 4/2014 Nishino et al.
2017/0002311 A1 1/2017 Otani et al.
2017/0253907 A1 9/2017 Aihara et al.

FOREIGN PATENT DOCUMENTS

| | | | |
|---|---|---|---|
| EP | 2878664 A1 | 6/2015 | |
| GB | 2192171 B * | 7/1990 | ............ A01N 25/26 |
| JP | S63-173580 A | 7/1988 | |
| JP | 2000-060450 A | 2/2000 | |
| JP | 2005-080607 A | 3/2005 | |
| WO | WO 1999/007466 A1 | 2/1999 | |
| WO | WO 2014/017513 A1 | 1/2014 | |
| WO | WO 2015/111685 A1 | 7/2015 | |
| WO | WO 2016/039391 A1 | 3/2016 | |

OTHER PUBLICATIONS

Japanese Patent Office, Written Opinion of the International Searching Authority in International Patent Application No. PCT/JP2017/026454 (dated Oct. 17, 2017).

Taiwanese Patent Office, Examination Report in Taiwanese Patent Application No. 106124529 (dated Jul. 28, 2021).

European Patent Office, Extended European Search Report in European Patent Application No. 17831138.7 (dated Jun. 19, 2019).

Capretto et al., "Micromixing Within Microfluidic Devices," *Top. Curr. Chem.*, 304: 27-68 (2011).

* cited by examiner (a)

(b)

(c)

(a)

(b)

METHOD AND DEVICE FOR PRODUCING LIQUID CULTURE MEDIUM COMPOSITION

CROSS-REFERENCE TO RELATED APPLICATIONS

This patent application is the U.S. national phase of International Patent Application No. PCT/JP2017/026454, filed Jul. 21, 2017, which claims the benefit of Japanese Patent Application No. 2016-144953, filed on Jul. 22, 2016, which are incorporated by reference in their entireties herein.

TECHNICAL FIELD

The present invention relates to a production method and a production device of a liquid medium composition. More particularly, the present invention relates to a production method and a production device, each capable of appropriately mixing at least two kinds of liquids (a first liquid containing particular compounds and a second liquid containing a substance that links the particular compounds to form a structure) to be mixed for forming the above-mentioned medium composition to produce a medium composition in which the above-mentioned structures are appropriately dispersed.

BACKGROUND ART

In recent years, techniques for proliferating or maintaining in vitro various organs, tissues and cells that play distinct roles in the body of animals and plants have been developed. Proliferation or maintenance of the organs and tissues in vitro is called organ culture and tissue culture, respectively, and proliferating, differentiating or maintaining in vitro the cells separated from an organ or tissue is called cell culture.

Cell culture is a technique for proliferating, differentiating or maintaining separated cells in vitro in a medium, and is indispensable for detailed analyses of the in vivo function and structure of various organs, tissues and cells.

In addition, the cells and/or tissues cultured by the technique are utilized in various fields including efficacy and toxicity evaluation of chemical substances, pharmaceutical products and the like, large-scale production of useful substances such as enzymes, cell proliferation factors, antibodies and the like, regenerative medicine supplementing organ, tissue and cells that were lost by disease and deficiency, improvement of plant breed, production of gene recombinant products, and the like.

As a medium for culturing cells and the like (organ, tissue, cells), a liquid culture medium can be mentioned, and the present inventors successfully developed a liquid medium composition enabling culture of cells and the like in a suspending state (patent documents 1 and 2).

The liquid medium composition described in patent document 1 is one in which particular compounds (particularly, a polymer compound having an anionic functional group) assemble via a divalent metal cation and the like to form amorphous structures, and the structures are dispersed in a liquid culture medium in a suspended state. In the following, the above-mentioned particular compound such as a polymer compound having an anionic functional group and the like is also referred to as a "particular compound", and a substance such as a divalent metal cation and the like which binds the particular compounds is also referred to as a "linking substance".

The medium composition provides a preferable liquid culture medium capable of culturing cells and the like in a suspended state without accompanying an operation such as shaking, rotation and the like having a risk of causing damage and loss of functions of cells and the like.

DOCUMENT LIST

Patent Documents patent document 1: WO 2014/017513
patent document 2: US-A-2014/0106348

SUMMARY OF THE INVENTION

Problems to be Solved by the Invention

The originally-intended preferable state of the liquid medium composition described in the above-mentioned patent document 1 is a state in which structures formed by coupling specific compounds with each other via a linking substance such as a divalent metal cation and the like are uniformly dispersed in the liquid culture medium.

However, the present inventors studied the actual production steps of the liquid medium composition in detail, and found that achieving such preferable state requires paying attention to the mixing method and mixing conditions to ensure that the structures are not unevenly formed locally in the medium composition.

For example, when the particular compound is deacylated gellan gum, it forms an indeterminate amorphous structure via a linking substance (e.g., calcium ion) in a liquid culture medium when mixed with the liquid medium, and the structure becomes a carrier for suspending cells and the like.

However, the methods described in patent documents 1 and 2 were used to produce a large amount of a medium composition and it was found that, in a mixing method including pouring a liquid containing a particular compound at a high concentration into a liquid culture medium containing a linking substance while stirring the medium, the particular compound contacts the linking substance at the moment the both liquids come into contact with each other to form structures, as a result of which the structures are sometimes linked to form a long string suspended in the mixture (or string structure entangled in a mass), which is not the originally-intended uniformly dispersed state. It was also found that such state is developed even when the mixture is stirred at a comparatively high speed. Once such string structure is formed in the liquid medium, it is not easy to cleave the structure finely and disperse same in the base material in view of the property of the structure that a double helix formed by the molecular chain forms a tight 3-dimensional network with each other via a linking substance (e.g., calcium ion).

To obtain a mixture in which the object structures are preferably dispersed, therefore, a special stirring apparatus is necessary to allow the both liquids to be contacted with each other at a high speed. However, the stirring action of such a special stirring apparatus is often generally limited to be effective for small amounts of liquids of about 1 L (L represents liter) or less, and the above structure is not suitable for producing a large amount (e.g., 5 L or more) of a mixture in which the above-mentioned structures are preferably dispersed. In addition, it was also found that the above-mentioned special stirring apparatus is configured to not permit mixing in a closed state, and thus cannot maintain a sterile condition with ease in a series of mixing processes and highly likely invites contamination of the medium composition by the outside air.

An object of the present invention is to solve the above-mentioned problem and provide a production method and a production apparatus capable of continuously and sterilely mixing any liquid containing a linking substance such as divalent metal cation and the like with a liquid containing particular compounds at any ratio and producing a large amount of the liquid medium composition comprising fine structures dispersed therein.

Means of Solving the Problems

The main constitution of the present invention capable of achieving the aforementioned object is as follows.

[1] A method for producing a liquid medium composition, comprising
  using a junction conduit structure having a structure in which a first inlet conduit and a second inlet conduit are joined together to form an outlet conduit, and
  flowing a first liquid containing a particular compound of the following (i) into the first inflow conduit and flowing a second liquid containing a linking substance of the following (ii) into the second inlet conduit, and allowing the flows of the both liquids to join together to mix the both liquids, thus forming the liquid medium composition comprising structures formed by the particular compound linked via the linking substance dispersed therein while being flown through the outlet conduit:
    (i) a particular compound which is a polymer compound having an anionic functional group, and capable of forming a structure by linking via a divalent metal cation, which structure being capable of suspending a cell or a tissue,
    (ii) a linking substance which is a divalent metal cation.

[2] The method for producing a liquid medium composition according to [1], wherein
  the particular compound of (i) is deacylated gellan gum, the first liquid is an aqueous solution containing deacylated gellan gum,
  the linking substance of (ii) is one or both of calcium ion and magnesium ion, and the second liquid is a liquid culture medium containing one or both of calcium ion and magnesium ion or a concentrated liquid of the liquid culture medium.

[3] The method for producing a medium composition according to [2], wherein a concentration of the deacylated gellan gum in the liquid medium composition is 0.001% (w/v) to 1.0% (w/v).

[4] The method for producing a medium composition according to any of [1] to [3], wherein, in the junction conduit structure,
  (a) the first inlet conduit and the second inlet conduit are aligned in a straight line such that the first liquid and the second liquid collide with each other facing opposite directions, and the outlet conduit extends forming a right angle to the first inlet conduit and the second inlet conduit, or
  (b) the first inlet conduit and the second inlet conduit are aligned in a V-shape such that the first liquid and the second liquid collide with each other forming a V-shape, and the outlet conduit extends from the confluence part in a direction dividing the internal angle of the V-shape into two equal portions.

[5] An apparatus for producing a liquid medium composition, the apparatus comprising:
  a junction conduit structure comprising a first inlet conduit and a second inlet conduit joined together to form an outlet conduit,
  a first liquid supply source connected to the aforementioned first inlet conduit for supplying a first liquid containing a particular compound of the following (i), and
  a second liquid supply source connected to the aforementioned second inlet conduit for supplying a second liquid containing a linking substance of the following (ii), wherein, in the aforementioned junction conduit structure,
  the first liquid supplied to the first inlet conduit and the second liquid supplied to the second inlet conduit are joined together to allow mixing of the both liquids, thus forming the liquid medium composition comprising structures formed by the particular compound linked via the linking substance dispersed therein while being flown through the outlet conduit:
    (i) a particular compound which is a polymer compound having an anionic functional group, and capable of forming a structure by linking via a divalent metal cation, which structure being capable of suspending a cell or a tissue,
    (ii) a linking substance which is a divalent metal cation.

[6] The production apparatus according to [5], wherein
  the particular compound of (i) is deacylated gellan gum, and the first liquid is an aqueous solution containing deacylated gellan gum,
  the linking substance of (ii) is one or both of calcium ion and magnesium ion, and the second liquid is a liquid culture medium containing one or both of calcium ion and magnesium ion or a concentrated liquid of the liquid culture medium.

[7] The production apparatus according to [6], wherein a concentration of the deacylated gellan gum in the liquid medium composition is 0.001% (w/v) to 1.0% (w/v).

[8] The production apparatus according to any of [5] to [7], wherein, in the junction conduit structure,
  (a) the first inlet conduit and the second inlet conduit are aligned in a straight line such that the first liquid and the second liquid collide with each other facing opposite directions, and the outlet conduit extends forming a right angle to the first inlet conduit and the second inlet conduit, or
  (b) the first inlet conduit and the second inlet conduit are aligned in a V-shape such that the first liquid and the second liquid collide with each other forming a V-shape, and the outlet conduit extends from the confluence part in a direction dividing the internal angle of the V-shape into two equal portions.

Effect of the Invention

In the following description, the mixed state of the first liquid and the second liquid is referred to as a "preferable mixed state" or an "unpreferable mixed state" depending on the dispersion state of the structures formed in the mixed liquid. The "preferable mixed state" is a state in which the structures are uniformly dispersed and continue to float in the mixed liquid of the first liquid and the second liquid. On the contrary, the "unpreferable mixed state" is a state in which the structures are not uniformly dispersed in the mixed liquid as described above but exist locally in a biased manner, for example, a state in which the structures float or sink in a long string-like manner in the mixed liquid, or a state in which the string-like structure floats or forms sediment in a locally entangled manner.

The dispersed state of the structure can vary steplessly from a preferable mixed state to an unpreferable mixed state. The state of the boundary between the preferable mixed state and the unpreferable mixed state, that is, the lower limit of the preferable mixed state, may be appropriately determined according to the intended use and by an evaluation method described later or the like.

According to the production method and the production apparatus of the present invention, the first liquid and the second liquid both flow in the respective conduits (the first inlet conduit and the second inlet conduit), join together in the junction conduit structure, collide with each other, and flow in the outlet conduit as a mixture. By the action of this joining, it is possible to form the liquid medium composition in a preferable mixed state as a flow in an outlet conduit by the feeding force of the liquid and the confluence structure of the junction conduit structure without using a stirrer for mixing (a movable member driven by an external power). Thus, according to the present invention, it is possible to continuously obtain intended amount or supplied amounts of the both liquids from the outlet conduit of the liquid medium composition, for example, from a small amount of an experimental medium composition to a large amount of a medium composition to fill a large industrial culture chamber.

The present invention showed for the first time, as regards two liquids that affords a mixture containing a structure formed by a particular compound linked via a linking substance, that a favorable mixed state is obtained by mixing by confluence as described above. Such mixing method is particularly useful when the first liquid is an aqueous solution containing deacylated gellan gum and the second liquid is a liquid medium containing one or both of calcium ion and magnesium ion.

Furthermore, for the production method and the production apparatus of the present invention, it is important that both of the first liquid and the second liquid flow at the time of joining. With this feature, even when the concentrations of the two liquids are different, the two liquids can be preferably joined together and mixed by adjusting the ratio of flow rate and the ratio of flow velocity of the two liquids. For example, when the concentration of the particular compound of the first liquid is low and the second liquid is a general liquid medium, the two liquids can be preferably mixed by joining the two liquids together by setting the flow rate and flow velocity of the first liquid and the second liquid to similar levels. Further, when the concentration of the particular compound of the first liquid is high and the second liquid is a general liquid medium, for example, the two liquids can be preferably mixed by adjusting the sectional area of the first conduit to reduce the ratio of the flow rate of the first liquid to that of the second liquid and joining the two liquids together while colliding them at a high speed. As described above, even when the concentration of the particular compound in the first liquid and the concentration of the linking substance in the second liquid vary over a wide range, the both liquids can be preferably mixed by changing the ratio of the flow rate and the flow velocity (particularly, ratio of flow rate).

In addition, in the production method and the production apparatus of the present invention, the both liquids can be more preferably mixed by adding a static mixer (commercially available member or flow path structure equivalent thereto) to the subsequent stage of the junction conduit structure.

In addition, according to the production method and the production apparatus of the present invention, as shown in FIG. 1, the first liquid and the second liquid can be moved, joined together, mixed with each other, and supplied aseptically to an object container or the like from respective sources without contacting with a contamination source such as the outside air and the like and without contacting an unnecessary member.

In addition, when a peristaltic pump is used as a pump for sending each of the first liquid and the second liquid, the connecting conduit and the junction conduit structure can be disposable, and maintenance such as cleaning of the inside of the conduit becomes unnecessary.

DESCRIPTION OF EMBODIMENTS

Hereinafter, the production method of the present invention is described in detail, reference is made to the production apparatus of the present invention, and the structure of the production apparatus is also described in detail.

The production method is a method for producing the liquid medium composition by mixing the first liquid containing a particular compound of the following (i) and the second liquid containing a linking substance of the following (ii).

(i) a particular compound which is a polymer compound having an anionic functional group, and capable of forming a structure by linking via a divalent metal cation, which structure being capable of suspending a cell or a tissue, (ii) a linking substance which is a divalent metal cation.

The details of the particular compound and linking substance, and the first liquid and the second liquid respectively containing them, and the liquid medium composition which is the mixture thereof are described later.

Figure 1:
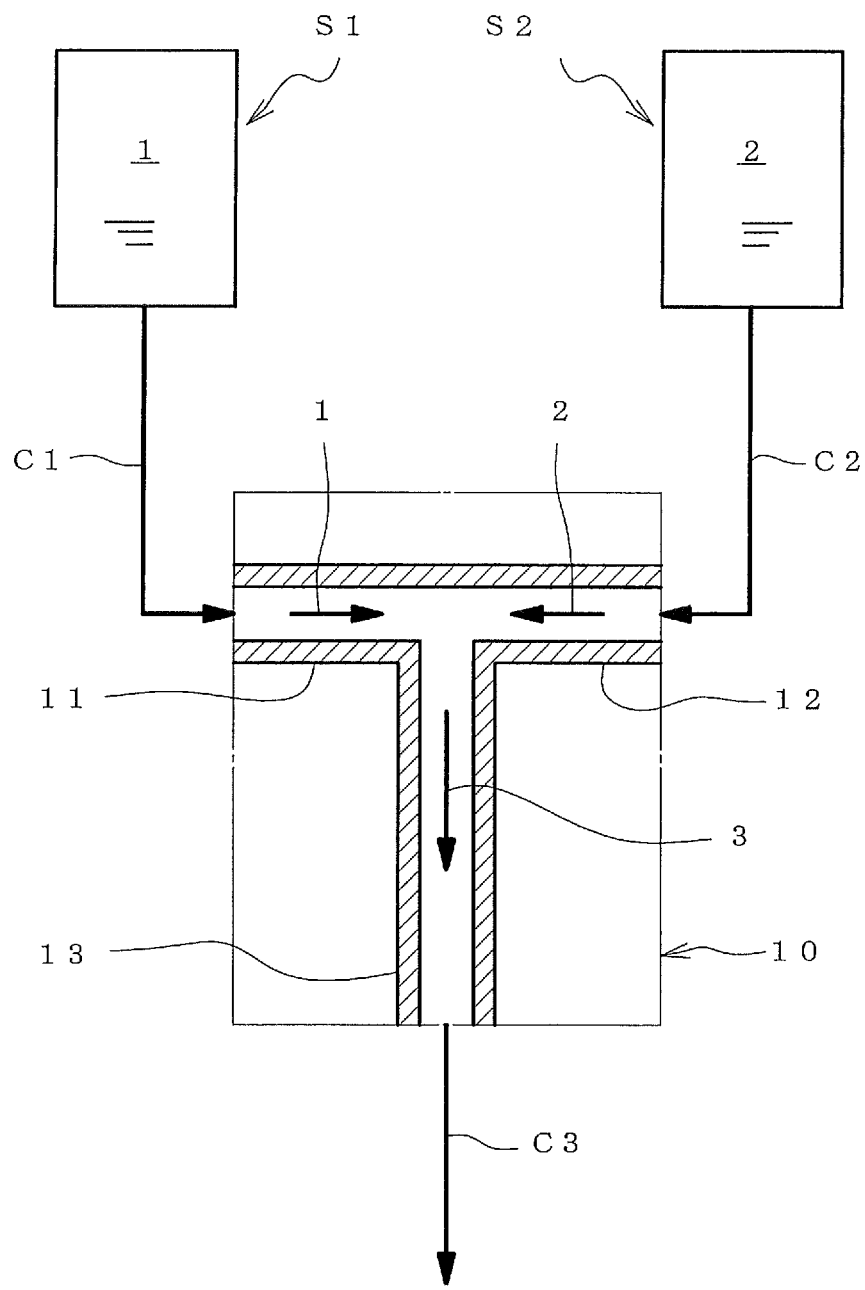
FIG. 1 is a schematic showing of the constitutions of the production method and production apparatus of the present invention. In this Figure, only the flow path in the junction conduit structure is shown as a sectional view for the sake of explanation.

As illustrated in FIG. 1, the production method employs a junction conduit structure 10 having a structure in which a first inlet conduit 11 and a second inlet conduit 12 are joined to form an outlet conduit 13. The junction conduit structure may have various structures as described below. Thus, in FIG. 1, the junction conduit structure 10 is generally represented by a dashed line, and the internal flow passage structure (junction structure) is typically depicted as a simple T-shaped junction conduit. The flow direction of each liquid is for illustrative purposes, and is not limited to the flow direction (horizontal direction or vertical direction) in the Figure (the same applies to other Figures). In the production method, the first liquid 1 containing the particular compound of (i) is fed to the first inlet conduit 11 and flowed, and the second liquid 2 containing the connecting substance (ii) is fed to the second inlet conduit 12 and flowed, and the flows of the two liquids are joined together to form a mixture (i.e., liquid medium composition for production purposes) 3 in which the two liquids are mixed in the outlet conduit 13. Consequently, a liquid medium composition in a preferred mixed state, in which the structures in which the particular compound is bound via the linking substance are dispersed, is obtained as a flow in the outlet conduit 13.

The production apparatus according to the present invention, as illustrated in FIG. 1, is an apparatus capable of carrying out the production method of the present invention and producing the liquid medium composition in a preferable mixed state. As illustrated in FIG. 1, the production apparatus includes the above-described junction conduit structure 10, and further includes a first liquid supply source S1 and a second liquid supply source S2.

The first liquid supply S1 is a device configured to supply the first liquid 1, which in the example of FIG. 1 contains at least a container containing the first liquid 1 and a device for delivering the first liquid 1. In FIG. 1, the first liquid supply S1 is depicted as a simple container, and the illustration of the device for delivering a liquid is omitted. The first liquid supply S1 is illustratively connected to the first inlet conduit 11 of the junction conduit structure 10 via a connecting pipe C1. Similarly, the second liquid supply S2 is a device configured to supply the second liquid 2. In the example of FIG. 1, the second liquid supply S2 has at least a container containing the second liquid 2 and a device for delivering the second liquid 2, the device for delivering the liquid being not shown, and is illustratively connected to the second inlet conduit 12 of the junction conduit structure 10 via a connecting pipe C2.

The supply conduit C3 connected to the outlet conduit 13 of the junction conduit structure 10 suggests a conduit for supplying the produced liquid medium composition 3 to a container or the like, and is not essential. The produced liquid medium composition 3 may be directly supplied from the exit of the outlet conduit 13 to a container or the like intended for use.

According to the above configuration, when the production apparatus is operated, the first liquid 1 supplied from the first liquid supply source S1 to the first inflow conduit 11 and the second liquid 2 supplied from the second liquid supply source S2 to the second inflow conduit 12 join and mix, thereby forming the liquid medium composition 3 in which the structure in which the particular compound is bound via the connecting substance is dispersed, and the liquid medium composition 3 flows out from the outlet conduit 13. Therefore, both the liquids 1 and 2 of the first and second liquid supply sources are supplied as the liquid medium composition 3 in a necessary amount and in a preferable mixed state without coming into contact with a contamination source such as the outside air.

First, the first liquid 1 containing the particular compound of the afore-mentioned (i), the second liquid 2 containing the linking substance of the afore-mentioned (ii), and a liquid medium composition (liquid in which a structure in which the particular compounds are linked via the linking substance(s) is dispersed) 3 formed by mixing these liquids are described in detail.

[The First Liquid]

The first liquid contains, as a particular compound, a polymer compound having an anionic functional group and capable of forming a structure that can suspend cells or tissues by binding via a divalent metal cation.

As the anionic functional group, a carboxy group, a sulfo group, a phosphate group and a salt thereof can be mentioned, with preference given to a carboxy group or a salt thereof. A polymer compound to be used in the present invention may contain one or more kinds selected from the group of the aforementioned anionic functional groups.

Specific preferable examples of the polymer compound to be used in the present invention include, but are not limited to, polysaccharides wherein not less than 10 monosaccharides (e.g., triose, tetrose, pentose, hexsauce, heptose etc.) are polymerized, more preferably, acidic polysaccharides having an anionic functional group. The acidic polysaccharide here is not particularly limited as long as it has an anionic functional group in the structure thereof, and includes, for example, polysaccharides having a uronic acid (e.g., glucuronic acid, iduronic acid, galacturonic acid, mannuronic acid), polysaccharides having a sulfate group or phosphate group in a part of the structure thereof, and polysaccharides having the both structures, and includes not only naturally-obtained polysaccharides but also polysaccharides produced by microorganisms, polysaccharides produced by genetic engineering, and polysaccharides artificially synthesized using an enzyme. More specifically, examples thereof include polymer compounds composed of one or two or more kinds from the group consisting of hyaluronic acid, gellan gum, deacylated gellan gum (hereinafter sometimes to be referred to as DAG), rhamsan gum, diutan gum, xanthan gum, carageenan, xanthan gum, hexuronic acid, fucoidan, pectin, pectic acid, pectinic acid, heparan sulfate, heparin, heparitin sulfate, keratosulfate, chondroitin sulfate, dermatan sulfate, rhamnan sulfate and a salt thereof. Polysaccharide is preferably hyaluronic acid, DAG, diutan gum, xanthan gum, carageenan or a salt thereof, more preferably DAG or a salt thereof. Phosphorylated DAG can also be used. The phosphorylation can be performed by a known method.

The salt here includes, for example, salts with alkali metals such as lithium, sodium, potassium; salts with alkaline earth metals such as calcium, barium, magnesium; and salts with aluminum, zinc, copper, iron, ammonium, organic base and amino acid, and the like.

The weight average molecular weight of these polymer compounds (polysaccharides etc.) is preferably 10,000 to 50,000,000, more preferably 100,000 to 20,000,000, still more preferably 1,000,000 to 10,000,000. For example, the molecular weight can be measured based on pullulan by gel penetration chromatography (GPC).

In the present invention, plural kinds (preferably two kinds) of the above-mentioned polysaccharides having an anionic functional group can be used in combination. A polysaccharide having an anionic functional group and a polysaccharide not having an anionic functional group may also be combined. The kind of the combination of the polysaccharides is not particularly limited as long as the aforementioned structure is formed in a liquid culture medium by linking via a divalent metal cation. Preferably, the combination includes at least DAG or a salt thereof. That is, a preferable combination of polysaccharides contains DAG or a salt thereof, and polysaccharides other than DAG and a salt thereof (e.g., xanthan gum, alginic acid, carageenan, diutan gum, methylcellulose, locust bean gum or a salt thereof). Examples of specific combination of polysaccharides include, but are not limited to, DAG and rhamsan gum, DAG and diutan gum, DAG and xanthan gum, DAG and carageenan, DAG and xanthan gum, DAG and locust bean gum, DAG and κ-carageenan, DAG and sodium alginate, DAG and methylcellulose, and the like.

The deacylated gellan gum is a linear high molecular weight polysaccharide containing 4 molecules of sugars of 1-3 bonded glucose, 1-4 bonded glucuronic acid, 1-4 bonded glucose and 1-4 bonded rhamnose as the constituent unit, which is a polysaccharide of the following formula (I) wherein $R_1$, $R_2$ are each a hydrogen atom, and n is an integer of two or more. $R_1$ may contain a glyceryl group, $R_2$ may contain an acetyl group, and the content of the acetyl group and glyceryl group is preferably not more than 10%, more preferably not more than 1%.

pound, it is generally water or hydrophilic solvent, preferably water. In a preferable embodiment, therefore, the first liquid is an aqueous solution of the particular compound.

The concentration of the particular compound contained in the first liquid is not particularly limited as long as, upon mixing with the second liquid, the particular compounds are linked via a divalent metal cation to form a structure capable of suspending cells or tissues in the mixture, the structure is uniformly dispersed in the mixture, and further, the finally-obtained liquid medium composition containing the structure can culture the cells or tissue in suspension. The concentration of the particular compound in the first liquid can be calculated from the concentration of the particular compound in the medium composition capable of culturing cells or tissues in suspension and the ratio of the volume of the first liquid to the volume of the medium composition obtained as the final product, as described in detail below. For example, when the first liquid with volume $V_1$ and the second liquid with volume $V_2$ are mixed to finally obtain a liquid medium composition with volume $V_1+V_2$, the concentration C % (w/v) of the particular compound in the

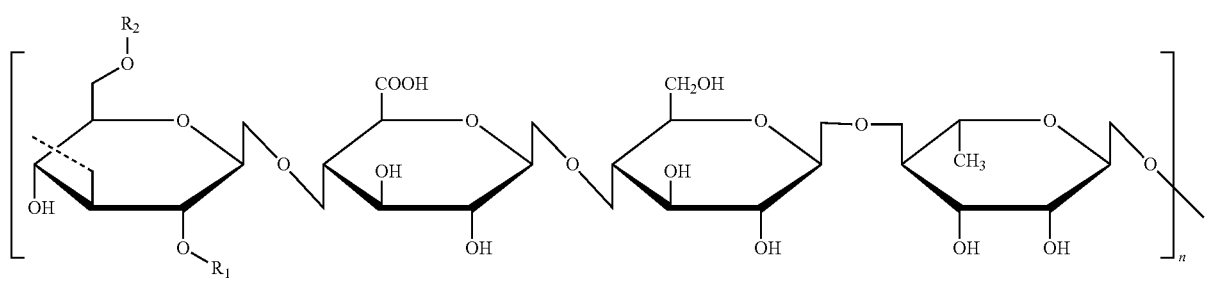

(I)

The particular compound may be obtained by a chemical synthesis method. When the particular compound is a naturally-occurring substance, it may be obtained from various plants, various animals, various microorganisms containing the compound by extraction, separation and purification by conventional techniques. For example, gellan gum can be produced by culturing producing microorganisms in a fermentation medium, recovering mucous products produced outside the bacterial cells by a general purification method, and, after the processes of drying, pulverizing and the like, powderizing the products. In the case of deacylated gellan gum, an alkali treatment should be applied when the mucous products are recovered, to deacylate the glyceryl group and the acetyl group bonded to 1-3 bonded glucose residue, and then the given products are recovered. Examples of the gellan gum-producing microorganism include, but are not limited to, *Sphingomonas elodea* and microorganism obtained by altering the gene of *Sphingomonas elodea*.

In the case of deacylated gellan gum, commercially available products, for example, "KELCAOGEL (registered trade mark of CP Kelco) CG-LA" manufactured by SAN-SHO Co., Ltd., "KELCOGEL (registered trade mark of CP Kelco)" manufactured by San-Ei Gen F.F.I., Inc. and the like can be used. As a native type gellan gum, "KELCOGEL (registered trade mark of CP Kelco) HT" manufactured by San-Ei Gen F.F.I., Inc. and the like can be used.

The first liquid is generally a solution of the particular compound. While the solvent for the solution is not particularly limited as long as it can dissolve the particular comliquid medium composition can be achieved by setting the concentration of the particular compound in the first liquid to $C \times (V_1+V_2)/V_1$ % (w/v).

The concentration of the divalent metal cation in the first liquid needs to be lower than the concentration at which the particular compound forms the structure in the first liquid. Examples of the divalent metal cation include calcium ion, magnesium ion, zinc ion, manganese ion, ferrous ion, copper ion and the like. Particularly, one or both of calcium ion and magnesium ion (hereinafter to be also referred to as "calcium ion and/or magnesium ion") contributes to the structure formation of a particular compound such as DAG and the like.

The first liquid may contain factors other than a particular compound and a solvent. Examples of the factor include, but are not limited to, physiologically acceptable buffering agent, salt, and isotonic agent.

The first liquid can be prepared by adding a particular compound to the above-mentioned solvent (e.g., water), stirring the mixture at a temperature capable of dissolving the particular compound (e.g., not less than 60° C., not less than 80° C., not less than 90° C.), and dissolving until a transparent state is formed. Using particular compound (DAG etc.) subjected to divalent metal cation-exclusion treatment, a dissolution operation is easy since it is dissolved in water without requiring heating. Where necessary, the obtained solution of the particular compound is subjected to a divalent metal cation-exclusion treatment to render the concentration of the divalent metal cation in the solution lower than the structure-forming concentration. Where necessary, a factor other than the particular compound may be added to the solvent in advance, or a factor other than the particular compound may be added to the obtained solution of the particular compound. The first liquid is preferably sterilized. Examples of the method of the sterilization include, but are not limited to, autoclave, filtration sterilization and the like.

[The Second Liquid]

The second liquid contains a divalent metal cation as a linking substance. Examples of the divalent metal cation include calcium ion, magnesium ion, zinc ion, manganese ion, ferrous ion, copper ion and the like. While the kind of the divalent metal cation is not particularly limited as long as the particular compound in the first liquid is bonded via a divalent metal cation to form a structure capable of suspending cells or tissues, with preference given to calcium ion.

The second liquid is generally a solution of a linking substance (i.e., divalent metal cation). While the solvent for the solution is not particularly limited as long as it can dissolve the particular compound, it is generally water or hydrophilic solvent, preferably water. In a preferable embodiment, therefore, the second liquid is an aqueous solution of a linking substance (i.e., divalent metal cation).

The second liquid contains a divalent metal cation in an amount that renders the concentration of the divalent metal cation in the final liquid medium composition obtained by mixing the first liquid and the second liquid sufficient for the particular compound in the first liquid to form a structure.

The divalent metal cation concentration of the second liquid can be calculated from the divalent metal cation concentration of the finally obtained liquid medium composition and the mixing ratio of the first liquid and the second liquid.

The second liquid may contain factors other than a linking substance (i.e., divalent metal cation) and the solvent. Examples of the factor include medium constituent components suitable for culturing the intended cells. Examples of the medium constituent component include, but are not limited to, buffering agent (carbonate buffer, phosphate buffer, HEPES etc.), inorganic salts (NaCl etc.), various amino acids, various vitamins (choline, folic acid etc.), saccharides (glucose etc.), antioxidants (monothioglycerol etc.), pyruvic acid, fatty acids, serum, antibiotics, insulin, transferrin, lactoferrin, cholesterol, various cytokines, various hormones, various growth factors, various extracellular matrices, and the like. The second liquid is preferably sterilized. Examples of the sterilization method include, but are not limited to, autoclave, filtration sterilization and the like.

In a preferable embodiment, the second liquid is a liquid medium containing divalent metal cation (preferably, calcium ion and/or magnesium ion) at the concentration allowing formation of a structure, or a concentrate of the medium.

According to the present invention, even when the particular compound concentration of the first liquid is high (i.e., the amount of the solvent (water) contained in the first liquid is small), it is possible to preferably mix the first liquid and the second liquid. Therefore, when the particular compound concentration of the first liquid is high and the first liquid is small, the dilution of the second liquid (liquid medium) by the first liquid can be ignored, so that the second liquid may be a liquid medium that can be used without being diluted, rather than a concentrate.

On the other hand, when the particular compound concentration of the first liquid is relatively low (i.e., when the amount of the solvent (water) contained in the first liquid is relatively large), the first liquid and the second liquid tend to be easily and preferably mixed, and the structure can be preferably dispersed. Therefore, when the particular compound concentration of the first liquid is low (when the amount of the solvent (water) is not negligible for the second liquid), it is preferable that the second liquid (liquid medium) be a concentrate that becomes a preferable liquid medium after mixing in consideration of dilution with the first liquid.

The second liquid contains medium constituent components suitable for culturing the intended cells in addition to divalent metal cation (preferably, calcium ion and/or magnesium ion) and water. The range of the concentrations of calcium ion and magnesium ion in a commonly used liquid medium for culturing cells is about 0.1-2.0 mM and 0.1-1.0 mM, respectively, and thus they are sufficient to allow DAG and the like to form a structure. The concentration of the divalent metal cation, preferably calcium ion and/or magnesium ion, in the second liquid is adjusted in consideration of the mixing ratio with the first liquid so that the concentration of divalent metal cations in the finally obtained liquid medium composition will be the structure formation concentration. The same applies to other linking substances. The concentration of the medium component suitable for culturing the intended cells in the second liquid is adjusted in consideration of the mixing ratio with the first liquid so that the concentration of the medium component in the finally obtained liquid medium composition will fall within a concentration range suitable for culturing the intended cells. For example, when a liquid medium composition having a volume of $V_1+V_2$ is finally obtained by mixing a first liquid having a volume of $V_1$ and a second liquid having a volume of $V_2$, the concentration of the divalent metal cation in the second liquid may be set to $Ci \times (V_1+V_2)/V_2$ to set the concentration of the divalent metal cation in the liquid medium composition to Ci. The same applies to other linking substances. Similarly, when the first liquid of volume $V_1$ and the second liquid of volume $V_2$ are mixed to finally obtain a liquid medium composition of the volume $V_1+V_2$, the concentration of the medium constituent component in the second liquid may be set to $Cm \times (V_1+V_2)/V_2$ to set the concentration of the medium constituent component in the liquid medium composition to Cm.

In this embodiment, the intended liquid medium composition containing a structure in which particular compounds contained in the first liquid are linked via a linking substance contained in the second liquid can be obtained immediately by mixing the first liquid and the second liquid according to the production method of the present invention.

The second liquid may not contain a part or the whole of the medium constituent component for cell culture. In this case, the intended liquid medium composition can be obtained by, in the production method of the present invention, mixing the first liquid and the second liquid to give a mixture containing a structure in which particular compounds contained in the first liquid are linked via a linking substance contained in the second liquid and adding a part or the whole of the above-mentioned liquid culture medium constituent component for cell culture to the mixture.

The volume mixing ratio of the first liquid and the second liquid is, for example, 10 to 9900, preferably 100 to 4900, of the volume of the second liquid with respect to the volume 100 of the first liquid.

In a preferable embodiment, 90 mole % or more (preferably 95 mole % or more, more preferably 99% or more, and most preferably 100%) of the particular compound contained in the liquid medium composition produced by the production method of the present invention is derived from the first liquid, and 90 mole % or more (preferably 95 mole % or more, more preferably 99% or more, and most preferably 100%) of the divalent metal cation contained in the medium composition is derived from the second liquid.

[Liquid Medium Composition]

The liquid medium composition that can be obtained by the production method of the present invention contains a structure in which particular compounds contained in the first liquid are linked via a linking substance (i.e., divalent metal cation) contained in the second liquid, wherein the structures are uniformly dispersed in the medium composition. Therefore, using the medium composition, cells and tissues can be cultured while maintaining the suspended state.

The type of organism from which cells or tissues to be cultured are derived is not particularly limited, and may be not only animals (insect, fish, amphibian, reptiles, birds, pancrustacea, hexapoda, mammals and the like) but also plants.

In one embodiment, the cell to be cultured is an anchorage dependent cell. Using the liquid medium composition that can be obtained by the production method of the present invention, anchorage dependent cells can be cultured while maintaining a suspended state, without using a carrier to be the anchorage.

Suspending of cells and/or tissues in the present invention refers to a state where cells and/or tissues may contact the bottom surface but do not adhere to a culture container (non-adhesive). Furthermore, in the present invention, when the cells and/or tissues are proliferated, differentiated or maintained, the state where the cells and/or tissues are uniformly dispersed and suspended in the liquid medium composition in the absence of a pressure on or vibration of the liquid medium composition from the outside or shaking, rotating operation and the like is referred to as "static suspension", and culturing of the cells and/or tissues in such condition is referred to as "static suspension culture". In the "static suspension", the duration of suspending includes not less than 5 min, not less than 1 hr, not less than 24 hr, not less than 48 hr, not less than 7 days and the like, though the duration is not limited thereto as long as the suspended state is maintained.

The medium composition that can be obtained by the production method of the present invention permits static suspension of cells and/or tissues at least on one point in the temperature range (e.g., 0-40° C.) capable of maintaining or culturing cells or tissues. The medium composition that can be obtained by the present invention permits static suspension of cells and/or tissues at least at one point in the temperature range of preferably 25-37° C., most preferably 37° C.

Whether or not static suspension is possible can be evaluated by, for example, uniformly dispersing the cells to be cultured in a medium composition to be evaluated at a concentration of $2 \times 10^4$ cells/ml, injecting 10 ml thereof in a 15 ml conical tube, standing the tube for at least not less than 5 min (e.g., not less than 1 hr, not less than 24 hr, not less than 48 hr, not less than 7 days) at a temperature of about 4° C. to 10° C., and observing whether the suspended state of the cells is maintained. When not less than 70% of the total cells are in a suspended state, it is concluded that the suspended state was maintained. Polystyrene beads (Size 500-600 μm, manufactured by Polysciences Inc.) may be used for evaluation instead of the cells.

In a preferable embodiment, in the liquid medium composition that can be obtained by the production method of the present invention, the viscosity thereof is not substantially increased by the contained above-mentioned structure. The terms "not substantially increasing the viscosity of the liquid" mean that the viscosity of the liquid does not exceed 8 mPa·s. In this case, the viscosity of the liquid (that is, the viscosity of the liquid medium composition that can be obtained by the production method of the present invention) is not more than 8 mPa·s, preferably not more than 4 mPa·s, more preferably not more than 2 mPa·s at 37° C. The viscosity of the liquid containing the structure can be measured under 37° C. conditions and using an E-type viscosity meter (manufactured by Toki Sangyo Co., Ltd., TV-22 type viscosity meter, model: TVE-22 L, corn roter: standard roter 1° 34'×R24, rotating speed 100 rpm).

The concentration of the particular compound in a liquid medium composition that can be obtained by the production method of the present invention depends on the kind of the particular compound, and can be appropriately determined within the range where the particular compound can form the aforementioned structure in a liquid medium composition, and can uniformly suspend (preferably statically suspend) the cells and/or tissues (preferably, without substantially increasing the viscosity of the liquid). In the case of DAG, it is 0.001% to 1.0% (w/v), preferably 0.003% to 0.5% (w/v), more preferably 0.005% to 0.3% (w/v), further preferably 0.01% to 0.05% (w/v), most preferably 0.01% to 0.03% (w/v). In the case of xanthan gum, it is 0.001% to 5.0% (w/v), preferably 0.01% to 1.0% (w/v), more preferably 0.05% to 0.5% (w/v), most preferably 0.1% to 0.2% (w/v). In the case of κ-carrageenan and locust bean gum mixture system, the total of the both compounds is 0.001% to 5.0% (w/v), preferably 0.005% to 1.0% (w/v), more preferably 0.01% to 0.1% (w/v), most preferably 0.03% to 0.05% (w/v). In the case of a native type gellan gum, it is 0.05% to 1.0% (w/v), preferably 0.05% to 0.1% (w/v).

When plural kinds (preferably two kinds) of the above-mentioned polysaccharides are used in combination as a particular compound, the concentration of the polysaccharides can be appropriately determined within a range where a combination of the polysaccharides can form the aforementioned structure in a liquid medium composition, and the cells and/or tissues can be uniformly suspended (preferably statically suspended) (preferably without substantially increasing the viscosity of the liquid). For example, when a combination of DAG or a salt thereof and polysaccharide other than DAG and a salt thereof is used, the concentration of DAG or a salt thereof is, for example, 0.005-0.02% (w/v), preferably 0.01-0.02% (w/v), and the concentration of polysaccharide other than DAG and a salt thereof is, for example, 0.0001-0.4% (w/v), preferably 0.005-0.4% (w/v), more preferably 0.1-0.4% (w/v). Specific examples of the combination of the concentration range include the following.

DAG or a salt thereof: 0.005-0.02% (preferably 0.01-0.02%) (w/v)
polysaccharide other than DAG
xanthan gum: 0.1-0.4% (w/v)
sodium alginate: 0.0001-0.4% (w/v) (preferably 0.1-0.4% (w/v))
native gellan gum: 0.0001-0.4% (w/v)
locust bean gum: 0.1-0.4% (w/v)
methylcellulose: 0.1-0.4% (w/v) (preferably 0.2-0.4% (w/v))
carageenan: 0.05-0.1% (w/v)
diutan gum: 0.05-0.1% (w/v)

In one embodiment, a combination of deacylated gellan gum or a salt thereof and acidic polysaccharide or a salt thereof capable of maintaining a random coiled state in a divalent metal cationic medium and cross-linking via a divalent metal ion is used as the particular compound. The acidic polysaccharide is preferably any selected from the group consisting of alginic acid, pectin and pectic acid, more preferably alginic acid. The salt includes salts of alkali metals such as lithium, sodium, and potassium; salts of alkaline earth metals such as calcium, barium, and magnesium; salts of aluminum, zinc, copper, iron, and the like; ammonium salts and the like, with preference given to sodium salt. As the acidic polysaccharide or a salt thereof, sodium alginate is suitably used. In this embodiment, the concentration of deacylated gellan gum or a salt thereof in a liquid medium composition that can be obtained by the production method of the present invention is, for example, 0.002 to 0.01 (w/v) %, preferably 0.002 to 0.009 (w/v) %, more preferably 0.003 to 0.009 (w/v))%, and the concentration of the acid polysaccharide or its salt (e.g., sodium alginate) is, for example, 0.004 to 0.1 (w/v) %, preferably 0.004 to 0.02 (w/v) %, more preferably 0.004 to 0.015 (w/v))%, more preferably 0.005 to 0.015 (w/v))%.

The concentration can be calculated by the following formula.

Concentration [% ($w/v$)]=weight ($g$) of particular compound/cubic volume ($mL$) of medium composition×100

In a preferable embodiment, DAG or a salt thereof is used as the particular compound, and calcium ion is used as the linking substance. The first liquid is an aqueous solution containing DAG or a salt thereof. The second liquid is a concentrate of a liquid medium containing calcium ions. As the volume mixing ratio of the first liquid to the second liquid, as described above, the volume ($V_2$) of the second liquid to the volume ($V_1$) 100 of the first liquid is 10 to 9900, preferably 100 to 4900. The concentration of the DAG in the liquid medium composition obtained as a result of mixing is preferably 0.01% to 0.05% (w/v), most preferably 0.01% to 0.03 (w/v). The concentration of the calcium ion in the liquid medium composition obtained as a result of mixing is the concentration at which the DAG forms a structure, and is usually about 0.1 to 2.0 mM. The concentration of the medium constituent components in the liquid medium composition resulting from mixing is within a concentration range suitable for culturing the intended cells, e.g., mammalian cells.

The DAG concentration in the first liquid is the concentration obtained by multiplying the DAG concentration in the liquid medium composition resulting from the mixing described above by ($V_1+V_2$)/$V_1$ (i.e., 110/100 to 10000/100, preferably 200/100 to 5000/100).

The concentration of the calcium ion in the second liquid is the concentration obtained by multiplying the concentration of the calcium ion in the liquid medium composition obtained as a result of the mixing described above by ($V_1+V_2$)/$V_2$ (i.e., 110/10 to 10000/9900, preferably 200/100 to 5000/4900).

The concentration of the medium component in the second liquid is the concentration obtained by multiplying the concentration of the medium component in the liquid medium composition obtained as a result of the mixing described above by ($V_1+V_2$)/$V_2$ (i.e., 110/10 to 10000/9900, preferably 200/100 to 5000/4900).

Since the liquid medium composition contains a structure in which DAG is linked via a calcium ion uniformly dispersed therein, the cells and/or tissues can be uniformly suspended (preferably statically suspended) without substantially increasing the viscosity.

Using the liquid medium composition obtained by the production method of the present invention, cells and/or tissues can be cultured in a suspended state without an operation such as shaking, rotation and the like having a risk of causing damage and loss of functions of cells and tissues. Furthermore, using the medium composition, the medium can be exchanged easily during culture, and the cultured cells and/or tissues can also be recovered easily. Using the medium composition, adhesive cells can be prepared efficiently in a large amount without impairing the function thereof, since cells conventionally required to be cultured on a plate in a single layer in an adhered state to a cell container can be cultured in a suspended state.

The mixture of the first liquid and the second liquid may itself be a medium composition for production, or may be a medium composition for production by further adding an additive to the mixture.

Next, the junction conduit structure in the production method and the production apparatus of the present invention is described in detail. As shown in FIG. 1, the junction conduit structure having a structure in which the first inflow conduit 11 and the second inflow conduit 12 are joined to form an outlet conduit 13 and which is constituted such that the first liquid 1 and the second liquid 2 are mixed by joining may be used as the joining conduit structure. The joining conduit structure may be a flow path structure in which two inflow conduits join together simply, such as a T-shaped conduit or a Y-shaped conduit, or may be a structure in which one or both of the first inlet conduit and the second inlet conduit are joined together at one point, and the first liquid 1 and the second liquid 2 flowing in from the respective inflow conduits collide at one point, and flow out to the outlet conduit as a mixture (i.e., central collision type mixer). In addition, the junction conduit structure may have a structure in which the two liquids can be joined together to have a higher degree of mixing by only the structure of the flow path without using a movable stirrer, or may have a flow path structure in which not only the first liquid and the second liquid but also other liquids can be joined together and mixed as necessary.

Figure 2:
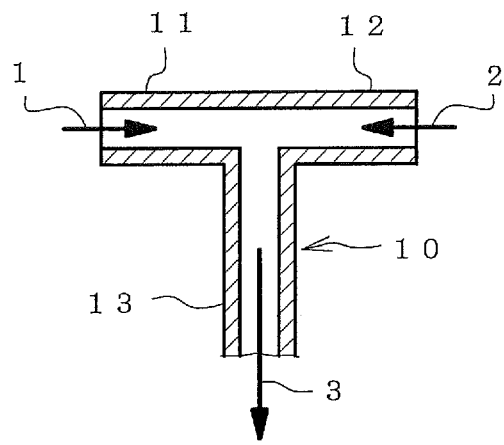
FIG. 2 is a sectional view showing a preferable embodiment of the junction conduit structure in the present invention.
Figure 2:
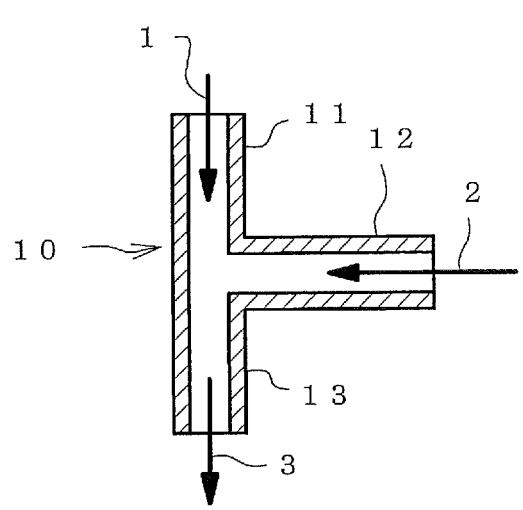
Figure 2:
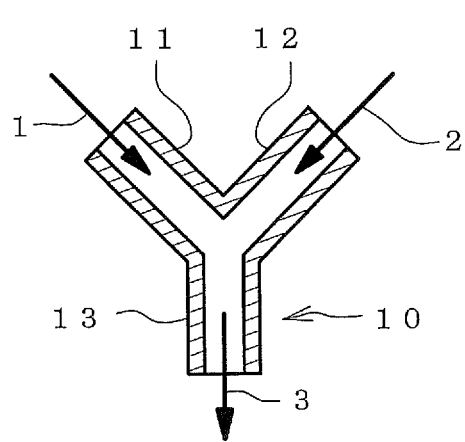

FIG. 2 is a sectional view illustrating a junction conduit structure in which two inlet conduits simply join together. FIGS. 2($a$) and 2($b$) show a simplified cross section of the T-shaped junction conduit structure 10, and FIG. 2($c$) shows a simplified cross section of the Y-shaped junction conduit structure. The structure of the joint for connection with the external conduit, such as screws or couplings, may be provided as appropriate. The attitude of each part of the conduit shown in the figure is for explanation.

In the embodiment of FIG. 2($a$), as in the schematic view of FIG. 1, one horizontal conduit located at the top of the T-shape in the Figure consists of two inflow conduits 11, 12, and the conduit extending downwards from the central junction constitutes an outlet conduit 13. The first liquid 1 and the second liquid 2, which flow into the inlet conduits 11 and 12, respectively, join together at a central confluence part and mix with each other, flow as a mixed liquid (liquid medium composition to be produced) 3 in the outlet conduit 13, and are discharged for supply. In this embodiment, the first inlet conduit 11 and the second inlet conduit 12 are aligned such that the first liquid 1 and the second liquid 2 collide with each other in position opposite directions, and the outlet conduit 13 extends at right angles to the first inlet conduit 11 and the second inlet conduit 12. As a result, the two liquids 1 and 2 collide violently with each other and mix with each other. In addition, a phenomenon in which both liquids flow into the outlet conduit 13 as a laminar flow does not occur.

The embodiment of FIG. 2(*b*) is a modification of the T-shaped flow path structure shown in FIG. 2(*a*), and horizontal conduits 11 and 12 located at the top of the T-shape shown in FIG. 2(*a*) are used as vertical conduits in FIG. 2(*b*) to form an inlet conduit 11 and an outlet conduit 13. The T-shaped vertical conduit 13 in FIG. 2(*a*) is the horizontal inflow conduit 12 in FIG. 2(*b*).

In the embodiment of FIG. 2 (*c*), the two slant lines located at the top of the Y-direction are the first and second inlet conduits 11, 12, which join together to form a downwardly extending outlet conduit 13.

Figure 3:
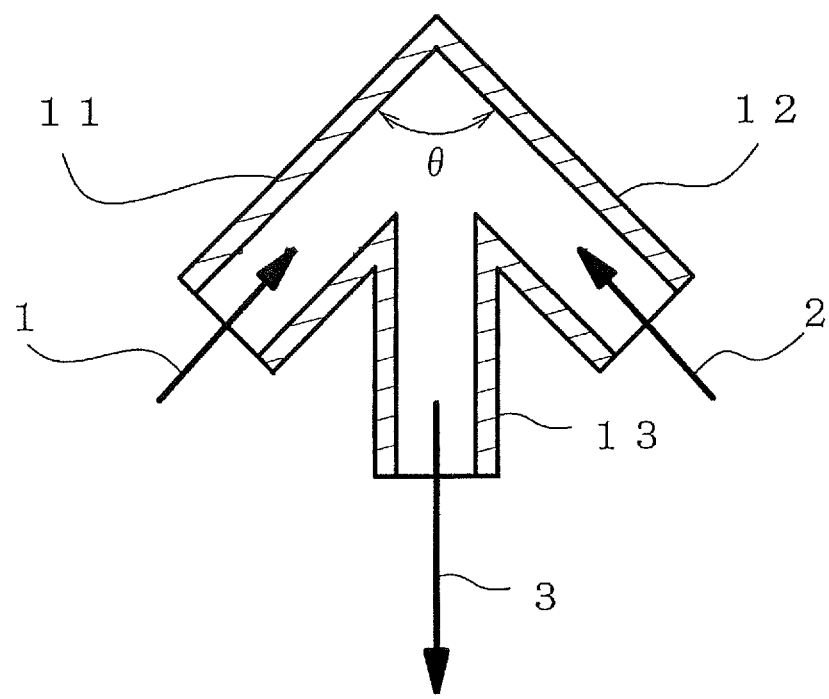
FIG. 3 is a sectional view showing another preferable embodiment of the junction conduit structure in the present invention.

FIG. 3 is a sectional view illustrating another embodiment of the junction conduit structure 10.

In the embodiment of FIG. 3, the first inlet conduit 11 and the second inlet conduit 12 are aligned in a V-shape such that the first liquid 1 and the second liquid 2 collide with each other in a V-shape, i.e., at a predetermined internal angle $\theta$. The two liquids 1 and 2 collide with each other at an angle, which is the same as the Y-shaped junction conduit structure of FIG. 2(C). However, in the embodiment of FIG. 3, the outlet conduit 13 extends from the joining to within the range of the V-shaped internal angle $\theta$, and in the more preferable embodiment extends in a direction that divides the V-shaped internal angle $\theta$ by two equal portions, contrary to the Y-shaped synchronous conduit structure. As a result, the two liquids 1 and 2 vigorously collide with each other and mix with each other in the same manner as in the T-shaped junction conduit structure of FIG. 2(*a*). Furthermore, since the outlet conduit 13 is located on the side of the internal angle between the first inlet conduit 11 and the second inlet conduit 12, a phenomenon that both liquids 1 and 2 flow into the outlet conduit 13 as laminar flows does not occur.

As illustrated in FIGS. 2(*a*) to 2(*c*) and FIG. 3, even in the flow path structure in which the two conduits join together simply, if the two liquids collide with each other to generate turbulent flow, the first liquid and the second liquid can be mixed in a preferable mixed state. These flow path structures are only typical examples of joining, and the number of conduits confluence and the angle between them are not limited to these examples, and are preferably selected so that the first liquid and the second liquid are mixed in a preferable mixed state.

Figure 4:
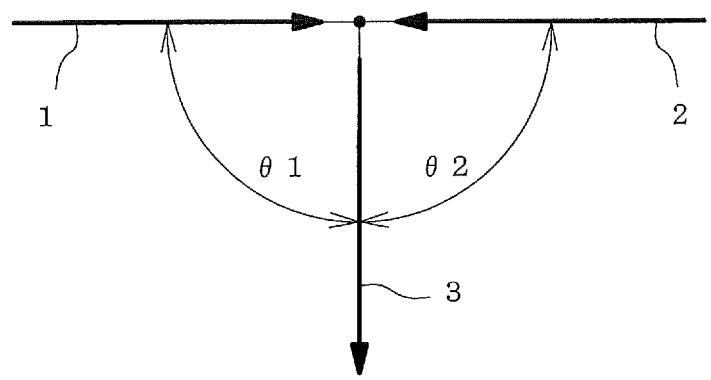
FIG. 4 is a schematic showing of a preferable collision state of the first and the second liquids in the junction conduit structure in the present invention.
Figure 4:
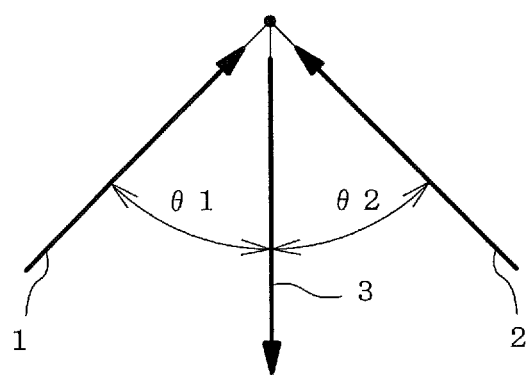

FIG. 4 is a schematic diagram illustrating a preferable collision state of the first and second liquids in the junction conduit structure according to the present invention. FIG. 4(*a*) corresponds to FIG. 2(*a*), and FIG. 4(*b*) corresponds to FIG. 3. To obtain a preferable mixed state of both liquids, it is preferable that the first liquid 1 and the second liquid 2 collide with each other in opposite directions, as shown in FIG. 4(*a*), or they collide with each other in a V shape, as shown in FIG. 4(*b*). In either case, the angle $\theta 1$ formed by the flow of the first liquid 1 and the flow of the mixed liquid 3 and the angle $\theta 2$ formed by the flow of the second liquid 2 and the flow of the mixed liquid 3 are preferably 30 degrees to 90 degrees, respectively. For example, in the T-shaped flow path of FIG. 4(*a*), the angles $\theta 1$ and $\theta 2$ are preferably 90 degrees. In the V-shaped flow path of FIG. 4(*b*), the inner angle of the V-shape is a sum of $\theta 1$ and $\theta 2$. $\theta 1$ and $\theta 2$ are preferably 10 degrees to 60 degrees, and $\theta 1=\theta 2$ is preferable.

When the angles $\theta 1$ and $\theta 2$ exceed 90 degrees as in the Y-shaped flow path structure shown in FIG. 2(C), the two liquids tend to smoothly join each other to form a laminar flow, and therefore, there is a case where a preferable mixed state is not obtained.

The junction conduit structure may have a structure in which both liquids 1 and 2 flowing in from the first and second inlet conduits are joined together and mixed such that a swirling flow is generated.

For example, if one liquid is combined with the other liquid in an outlet conduit such that the one liquid is a swirling flow surrounding the other liquid flowing centrally, the two liquids can be effectively mixed and a favorable mixed state. Alternatively, the joining conduit structure may be configured such that the two liquids join together at equal angles to each other such that both liquids form a swirling flow, such as a double helix. Alternatively, a structure may be employed in which a plurality of first inflow conduits and a plurality of second inflow conduits join together to generate a swirling flow.

The ratio of the flow velocities or flow rates of the first and second liquids in the case of generating the swirling flow can be appropriately determined in accordance with the concentration of the particular compound of the first liquid and the concentration of the linking substance of the second liquid so as to obtain a preferable mixed state.

Figure 5:
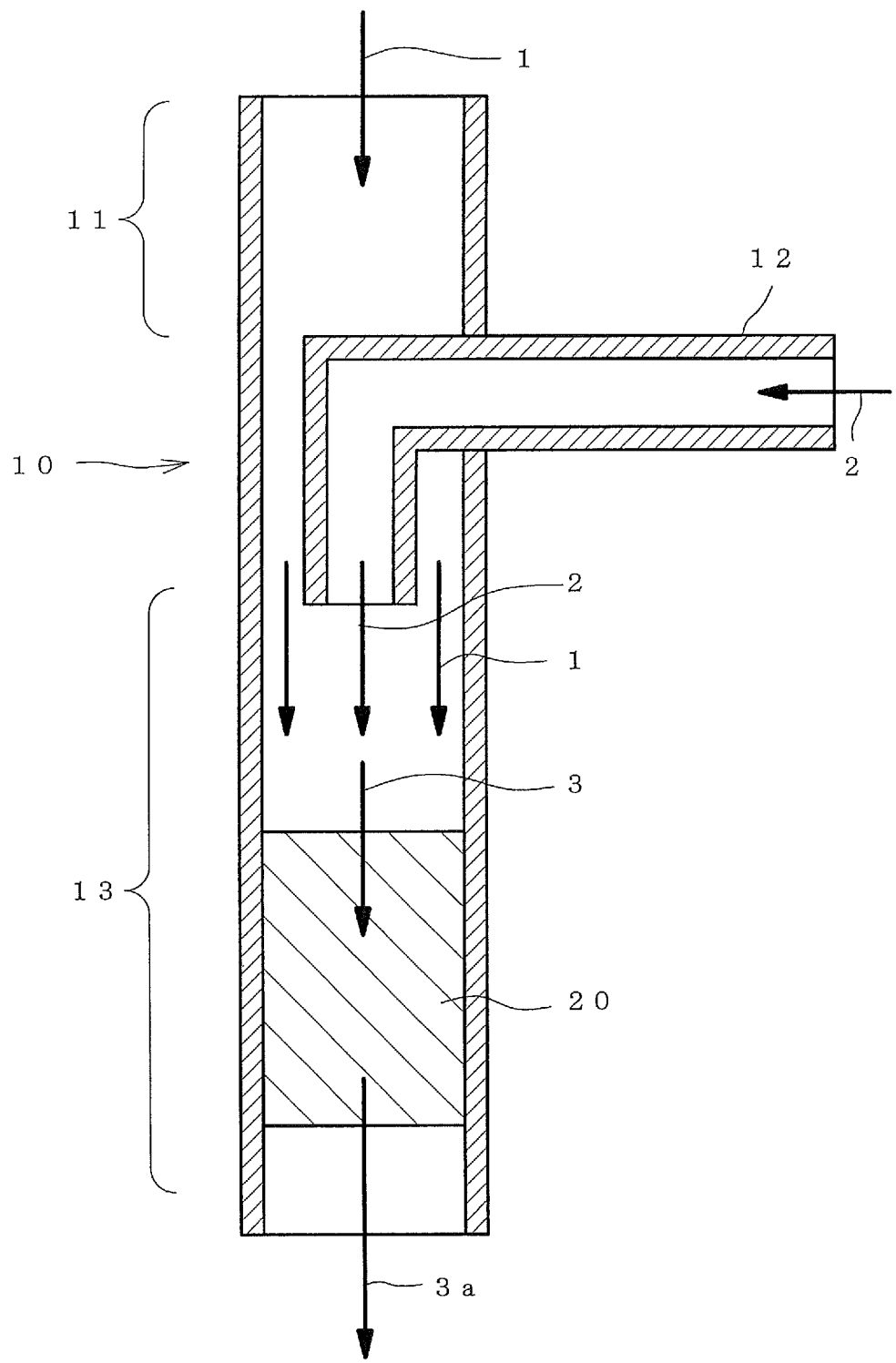
FIG. 5 is a sectional view showing another preferable embodiment of the junction conduit structure in the present invention.

FIG. 5 is a sectional view illustrating another embodiment of the junction conduit structure, showing an example in which two inlet conduits join together as a double pipe. In the embodiment of FIG. 5, the two liquids are arranged to join together so that the first liquid 1 is a central flow and the second liquid 2 is an outer flow concentrically surrounding said central flow. In this embodiment, the directions of flow of both liquids are the same. The central flow may be a liquid of one of the first liquid and the second liquid, and the other liquid may be an outer flow.

Even with such concentric joining, it is possible to obtain a favorable mixed state by preventing both liquids from remaining in laminar flow, such as by increasing the difference in velocity between the two liquids, or by disposing a member for generating turbulence in the flow path.

In a particular aspect of the invention, the junction of the tips of one of the inlet conduits may be narrowed in a nozzle-like manner, so that one liquid is injected at high speed into the other liquid flowing in the other inlet conduit, thereby causing the two liquids to join and mix. For example, in the junction conduit structure shown in FIG. 5, the outlet of the tip of the first inlet conduit 1 is narrowed in a nozzle shape. As a result, the first liquid enters the second liquid stream in the same direction as a flow having a very high flow velocity of about 2 to 50 times the flow velocity of the second liquid 2 and as a flow having a narrow and proper ratio, and the two liquids join together. Even if the two liquids are in impact contact with each other at such a large velocity difference, the two liquids are preferably mixed together in the outlet conduit 13. The length of the outlet conduit may be sufficiently long so that sufficient mixing can be obtained by joining and a stable flow can be obtained.

For example, when the flow velocity of the first liquid is about 0.5 mL/min to 10 L/min and the flow velocity of the second liquid is about 10 mL/min to 10 L/min in the joining conduit configuration shown in FIG. 5, the sectional area of the nozzle portion (the sectional area of the flow path when cut perpendicularly to the central axis line (flow-direction axis line) of the nozzle portion) may be determined in accordance with the flow velocity in order to join the two liquids at the large flow velocity difference as described above, and for example, about 0.01 mm$^2$ to 5.00 mm$^2$, preferably about 0.05 mm² to 2.00 mm², more preferably about 0.10 mm² to 0.70 mm² can be given. The cross-section of the nozzle portion is a cross-section taken perpendicular to the central axis of the nozzle portion. There is a relationship Q=SxV between the flow rate Q of the liquid passing through the exit of the nozzle section, the sectional area S of the nozzle section, and the flow velocity V of the liquid passing through the nozzle section.

Even in the special embodiment in which the above-mentioned large flow velocity difference is caused to join together, the concentration of the particular compound of the first liquid and the concentration of the linking substance of the second liquid are not particularly limited, and may be in the above-mentioned range.

The first and second inlet conduits and the outlet conduit are preferably flow paths through which liquid can flow without contacting the outside air. The first and second inflow and outlet conduits may be not only conduit embodiments as illustrated in FIGS. 2(a)-(c) and FIG. 3, but may also be flow passages formed in a mass of structural material that partially contains a large space.

As a material of the junction conduit structure, a material for structure having corrosion resistance and not affecting both liquids, such as metal, glass (silicate glass, etc.), plastic, etc., can be used.

When the two liquids are mixed by merging, it is preferable to appropriately select the concentration of the particular compound in the first liquid, the concentration of the linking substance in the second liquid, the ratio of the flow velocities of the two liquids, and the ratio of the flow velocities so that the mixed liquid can easily be brought into a preferable mixed state.

Hereinafter, for the purpose of explanation, a preferable combination of the concentration, the flow velocity, and the flow velocity of both liquids will be exemplified in the case where the particular compound of (i) is DAG, the first liquid is an aqueous solution containing the deacylated gellan gum, the linking substance of (ii) is calcium ion, and the second liquid is a liquid medium containing calcium ion.

First, the concentration of DAG in the liquid medium composition formed by mixing is preferably about 0.01% (w/v) to 0.05% (w/v), more preferably 0.01% (w/v) to 0.03% (w/v). The concentration of the calcium ion in the liquid medium composition obtained as a result of mixing is the concentration at which the DAG forms a structure, and is usually on the order of 0.1 to 2.0 mM.

The volume mixing ratio of the first liquid and the second liquid may be appropriately determined in accordance with the concentration of the particular compound and the concentration of the linking substance so as to obtain the target concentration of DAG in the liquid medium composition. In the present invention, since both liquids are mixed while flowing, the volume mixing ratio can also be expressed as a ratio of the flow velocity, the volume of liquid flowing per unit time.

For example, when the flow velocity ($FV_1$) of the first liquid is 100, the ratio of the flow velocity ($FV_2$) of the second liquid to that is usually 10 to 9900, preferably 100 to 4900.

The DAG concentration in the first liquid is the concentration obtained by multiplying the DAG concentration in the liquid medium composition resulting from the mixing described above by $(FV_1+FV_2)/FV_1$ (i.e., 110/100 to 10000/100, preferably 200/100 to 5000/100).

The concentration of the calcium ion in the second liquid is the concentration obtained by multiplying the concentration of the calcium ion in the liquid medium composition resulting from the mixing described above by $(FV_1+FV_2)/FV_2$ (i.e., 110/10 to 10000/9900, preferably 200/100 to 5000/4900).

The sectional areas of the first and second inlet conduits and the outlet conduits (the sectional areas of the conduits (flow paths) when cut perpendicularly to the central axis (axis in the flow direction) of the respective conduits), the flow rates and flow velocities of the first and second liquids, and the flow velocity of the mixed liquid are not particularly limited, and may be appropriately determined according to the required amount of the liquid medium composition from a small amount for experimental use to a large amount for industrial use (for example, when a liquid medium composition is filled in a large-volume container and sold, or for use in which a liquid medium composition is formed and supplied to a large-volume culture container in situ in a commercial cell culture field).

A general specific example is given. The sectional areas of the first and second inflow conduits are about 0.0075 mm² to 20 mm² (when the sectional shape is circular, the inner diameter is about 0.1 mm to 5 mm), the flow rate of the first liquid is about 0.5 mL/min to 10 L/min, and the flow rate of the second liquid is about 10 mL/min to 10 L/min. The sectional area of the outlet conduit can be determined according to the sectional areas of the first and second inlet conduits, and is about 0.0075 mm² to 400 mm² (when the sectional shape is circular, the inner diameter is about 0.1 mm to 200 mm), and the flow rate of the mixed liquid is the sum of the flow velocities of the first and second liquids. The flow rate of each liquid may be determined according to the capacity of each pump to deliver each liquid. A plurality of pumps may be used in parallel to increase the flow rate.

The sectional areas of the first and second inlet conduits and the outlet conduits are overall and average values, and when it is necessary to locally increase or decrease the flow velocity, the sectional areas of the conduits in the portions may be appropriately changed.

The flow velocity of each of the first and second liquids and the mixed liquid is determined by the flow rate of the liquid flowing through each of the above-mentioned conduits and the sectional area of each of the conduits (flow velocity=flow rate/sectional area). In the present invention, since the first and second liquids flow together and mix with each other, a certain high flow velocity is required. Such a high flow velocity can be achieved, for example, when the flow rate of the first liquid is on the order of 0.5 mL/min to 10 L/min and the flow rate of the second liquid is on the order of 10 mL/min to 10 L/min, by making the sectional areas of the first and second inflow conduits on the order of 0.01 mm² to 1.0 mm². Due to the high flow velocities thus obtained, the two liquids preferably collide with each other and mix.

Figure 6:
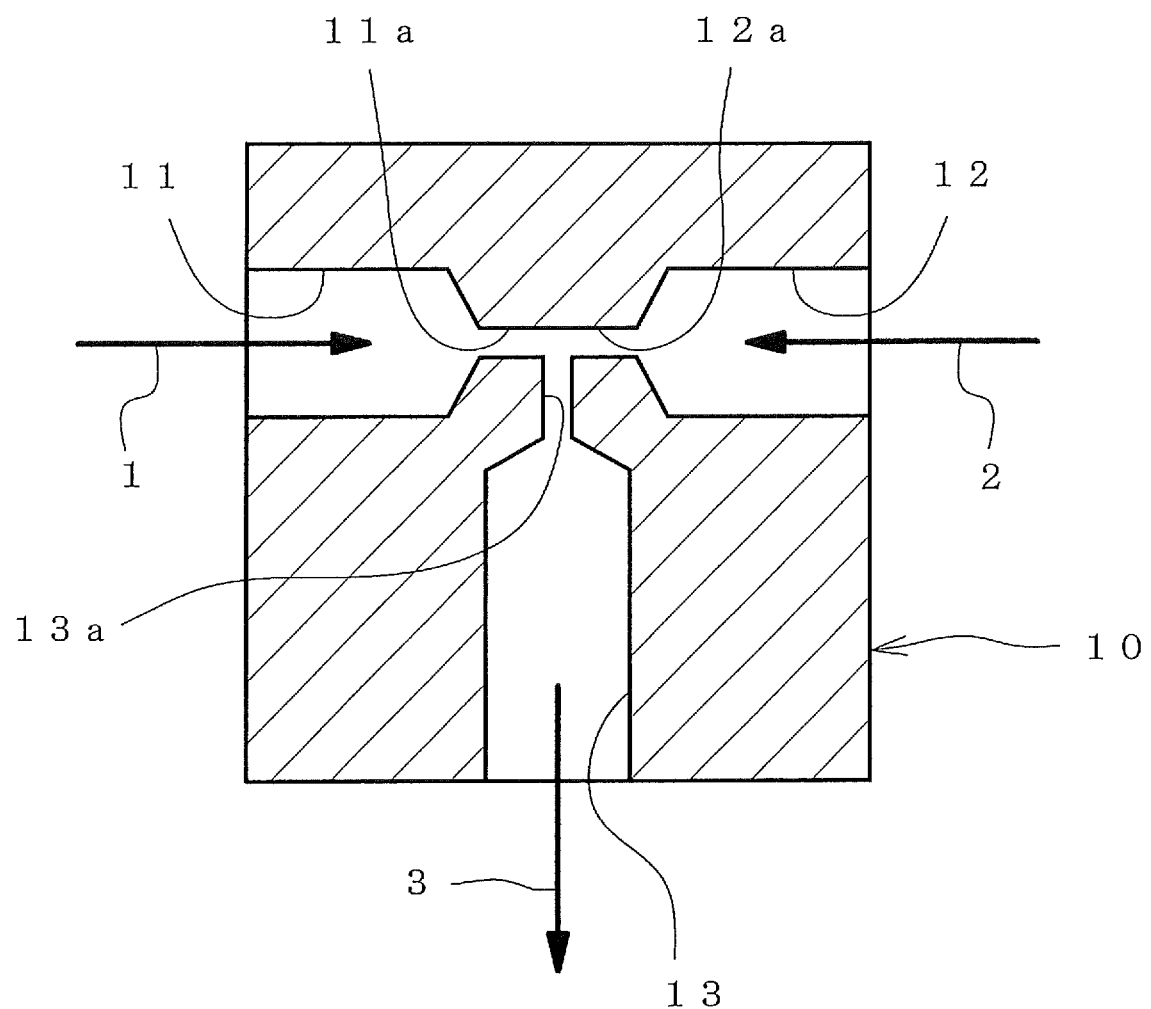
FIG. 6 is a sectional view showing a preferable embodiment of the joining part of the junction conduit structure in the present invention.

In the embodiment shown in FIG. 6, the sectional areas of the conduits (11a, 12a, 13a) of the respective confluence portions of the first conduit 11, the second conduit 12, and the outlet conduit 13 in the T-shaped confluence conduit structure 10 shown in FIG. 2(a) are reduced, and both liquids 1, 2 collide with each other at high speed and flow out to the outlet conduit 13 at high speed. Such an embodiment is also applicable to the V-shaped junction conduit structure 10 shown in FIG. 3. In this manner, the two liquids 1 and 2 are mixed in a violent collision to form a mixture 3 in a preferable mixed state.

It should be noted that the ratio of the flow velocities of the two liquids immediately before the joining may be about 100 to 10000, assuming that the flow velocity of the first liquid is 100. In addition, the flow velocity of the mixed liquid in the outlet conduit after the joining can be appropriately determined according to the respective flow path structures of the confluence conduit structure.

A static mixer (mixer having no movable agitation and configured to mix liquids by a flow path structure, also called a flow mixer, flow reactor, or microreactor) may be used as a structure that allows both liquids to be combined to achieve a higher degree of mixing. The static mixer may be the junction conduit structure itself or may additionally be provided after the junction conduit structure. The portion where the inlet conduit and the outlet conduit join may be a transient portion where it is not clear which of the first and second inlet conduits and the outlet conduit belong to.

In the example of FIG. 5, the static mixer element 20 is arranged so as to further enhance the degree of mixing of the joining liquid 3 after confluence with the first liquid 1 and the second liquid 2 (i.e., in the outlet conduit 13), and the outlet conduit 13 itself is a static mixer (i.e., the join together line structure includes a static mixer).

Alternatively, a static mixer may be connected after the outlet conduit 13. In such an alternative embodiment, the static mixer may be understood to be an outlet conduit. As shown in FIG. 5, by passing the combined liquid mixture 3 through the static mixer element 20, the mixed liquid 3 can be in a preferable mixed state due to its flow path structure.

It should be noted that coaxial joining as shown in FIG. may be a preferred input stream for static mixer elements where both liquids are not unevenly distributed. Therefore, when the static mixer element is used at the subsequent stage of the joining, it is preferable to appropriately select the flow path structure shown in FIGS. 2 and 3.

The mixing principle of the static mixer element or the static mixer, the channel structure for mixing itself, may refer to various structures known in the art.

For example, the "mixing vane member" described in JP-A-2010-264348 and the like is a typical static mixer element that repeatedly mixes the flow dividing and joining, and can be preferably used to further thoroughly mix the mixed liquid. Further, as a static mixer element for subdividing and confluence the mixed liquid flows to mix, a multi-layer structure called MSE (Multi Stacked Element) can be cited.

The junction conduit structure may have at least one of the following structures (i) to (iii), as in the above-described static mixer element or static mixer flow path structure.
  (i) A structure configured such that the flow of the mixed liquid of the first liquid and the second liquid mixed by the confluence of the first inlet conduit and the second inlet conduit passes through the division and the confluence one or more times in the outlet conduit.
  (ii) A structure configured such that the flow of the mixed liquid of the first liquid and the second liquid mixed by the joining of the first inlet conduit and the second inlet conduit becomes turbulent or swirling flow at the confluence part of the first inlet conduit and the second inlet conduit.
  (iii) A structure configured such that the first inlet conduit and the second inlet conduit are branched into two or more before joining each other, and the branched first inlet conduit and the branched second inlet conduit join each other, and join each other sequentially until finally becoming one outlet conduit. Such a structure enhances the degree of mixing by finely dividing the two liquids before merging, and by confluence the divided two liquids in a small amount at a large number of confluence portions. It may be determined as appropriate how many fine conversions are repeated to form a single outlet conduit. As such a structure, for example, a micromixer described in JP-A-2007-296452 can be cited.

In addition, examples of static mixers which can preferably mix the first liquid and the second liquid in small amounts include known mixers for microreactors (for example, Y-shaped, Helix type, Static type, etc. manufactured by YMC Co., Ltd.). These microreactor mixers are compact with conduits formed in the substrate.

The first liquid source has at least a container in which the first liquid is contained, and likewise the second liquid source has at least a container in which the second liquid is contained. Examples of the container include a rigid tank and a flexible bag made of a material capable of appropriately containing the first and second liquids. Preferably, the first liquid source and the second liquid source each have a pump for pumping liquid. The pump may be a feed device that can only be attached during operation of the production apparatus.

Pumps may utilize known liquid feed apparatuses, for example, pumps using pistons and cylinders (e.g., syringe pumps, bolmetric pumps, etc.), peristalsis pumps, etc., and devices capable of precision controlling flow rate, flow velocity, feed pressure, etc., are preferred. The capacity of the pump, such as the discharge amount and the discharge pressure, may be appropriately selected in accordance with the mixing of the two liquids described above.

If a peristaltic pump is used, the liquid in the respective conduits is not brought into contact with the outside air, and since the peristaltic pump itself does not have a conduit and does not require washing, if the used conduit is discarded, maintenance such as washing in the conduit becomes unnecessary. A peristaltic pump is a pump having a function of moving a liquid in a conduit line by moving a position where a pumping tube having elasticity and flexibility is crushed in a feeding direction, as typified by a tube pump (also called a roller pump).

The feeding capacity (flow rate per minute of the liquid moving in the tube) of the peristaltic pump is a wide range from a small flow rate to a large flow rate in a commercially available one, and is exemplified by about 0.01 (mL/min) to 10 (L/min). The pumping capacity of the peristaltic pump may be determined depending on the flow rate of each liquid to be combined, from laboratory to industrial. The peristaltic pump may form part of the production apparatus of the present invention or may be an external device to be utilized by the apparatus of the present invention.

When a peristaltic pump is used, it is preferable that the connection conduits C1 and C2 (conduits connecting the respective containers of the first and second liquid supply sources S1 and S2 and the junction conduit structure 10 to each other) in the production apparatus shown in FIG. 1 be tubes having a shape and a flexible portion that can be attached to the peristaltic pump as a pumping tube and that can function and operate as a pumping tube. Such a tube preferably has an inner diameter, an outer shape, and a length of the tube adapted to the peristaltic pump used, and has a softness that collapses when pressed against an actuator, such as a roller, of the peristaltic pump, and an elasticity that can return to its original shape when released from being pressed by the actuator. The connection tubes C1, C2 may be entirely pumping tubes, or only the part attached to the peristaltic pump may be pumping tubes.

EXAMPLES

Example 1

By carrying out the production method of the present invention using the production apparatus shown in FIG. 1, the first and second liquids were mixed at various concentrations and at various flow velocities, and the mixed state of the obtained medium composition (the dispersed state of the structure formed by the mixing of the two liquids) was evaluated.

[Constitution of Production Apparatus]

Plunger pumps (not shown) were used as the pumps of the first and second fluid sources S1, S2, and the respective plunger pumps were connected to the first and second inlet conduits 11, 12 of the junction conduit construction 10 using PTFE tubes (inner diameter 1.0 mm, outer diameter 1.6 mm, length 300 mm). To the exit of the outlet conduit 13, a PTFE tube (inner diameter: 1.0 mm, outer diameter: 1.6 mm, length: 500 mm) was connected.

For the junction conduit structure, as a T-shaped flow path structure shown in FIG. 6, a T-shaped mixer manufactured by Sanko Seiki Kogyo Co., Ltd. (made of stainless steel and having a sectional area of both the first and second inlet conduits at the junction of 0.20 mm$^2$) was used, and the first and second liquids were attached to allow collision with each other in the directions directly opposite to each other on a line.

[Adjustment of First Liquid and Second Liquid]

As the first liquid, 500 mL of an aqueous solution of deacylated gellan gum was prepared. As the second liquid, 500 ml of a concentrate of a DMEM liquid medium, a liquid medium containing calcium ion as a linking substance, was prepared. The concentration of deacylated gellan gum in the first liquid and the concentration rate of the DMEM liquid medium in the second liquid are shown in Table 1.

[Mixing]

The first and second liquids were respectively fed into the junction conduit structure at a predetermined flow rate (mL/min), mixed, and the resulting mixture was dispensed into a 50 mL conical tube (manufactured by Sumitomo Bakelite). Incidentally, the junction conduit structure and the flow path connected to the junction conduit structure were immersed in a constant temperature bath at 25° C. to adjust the temperature. The state of dispersion of the structure in the obtained mixture (liquid medium composition) was evaluated by the floatability of polystyrene beads.

Table 1 below shows the volume mixing ratio of the first liquid and the second liquid, the DAG concentration (% (W/v) of the first liquid, the concentration of the liquid medium that is the second liquid, the volume mixing ratio of both liquids, and the flow rate when both liquids are mixed.

The concentration of the second liquid is shown by the multiplication of the concentration, for example, "×2" (2-fold concentration), with the standard concentration as 1-fold.

TABLE 1

| | volume mixing ratio A:B | first liquid: total volume DAG concentration | second liquid: total volume concentration | flow rate (mL/min) |
|---|---|---|---|---|
| sample 1 | 1:1 | 500 mL 0.03% | 500 mL × 2 | A = 50 B = 50 |
| sample 2 | 1:3 | 250 mL 0.06% | 750 mL × 4/3 | A = 16.7 B = 50 |
| sample 3 | 1:9 | 100 mL 0.30% | 900 mL × 10/9 | A = 5.6 B = 50 |
| sample 4 | 1:19 | 50 mL 0.30% | 950 mL × 10/9 | A = 2.6 B = 50 |

The above-mentioned sample 1 is an example of joining a low concentration first liquid with a high concentration second liquid, the above-mentioned sample 2 is an example of joining a medium concentration first liquid with a medium concentration second liquid, and the above-mentioned samples 3 and 4 are examples of joining a high concentration first liquid with a standard concentration second liquid. In both cases, the sum of both liquids is 1000 mL.

In this example, to clarify the volume of each mixed liquid (i.e., mixing volume ratio), a predetermined amount of the first liquid and the second liquid are stored in each container of the first supply source and the second supply source (A:B=500:500, 250:750, 100:900), and each liquid is fed by a plunger pump until each container is empty.

[Evaluation of Mixed State]

Floatability: Immediately after mixing of both liquids, 10 mg of polystyrene beads (diameter of 600 μm, manufactured by Polysciences Corporation) were placed in the culture medium composition in conical tubes and mixed by inversion, and the floating state immediately after completing the inversion mixing and the floating state immediately after completing the inversion mixing again after 24 hours had elapsed after the completion of the inversion mixing were examined.

The criteria for evaluation of the floating state are as follows.

x: All beads are sedimented.

Δ: All beads float, but totally sink downward from the liquid level.

◯: All beads are suspended and do not tend to settle downwardly.

Visibility: The light transmittance after mixing and after one day was examined to obtain visibility.

The temperature at the time of mixing, the floatability after mixing, and the visibility are shown in Table 2 below.

TABLE 2

| | temperature during mixing | floatability (immediately after mixing) | floatability (one day later) | visibility (light transmission rate) |
|---|---|---|---|---|
| sample 1 | room temperature | X | Δ | 91.1% |
| sample 2 | room temperature | Δ | ◯ | 91.2% |
| sample 3 | room temperature | Δ | ◯ | 91.2% |
| sample 4 | room temperature | Δ | ◯ | 91.4% |

In the results of Table 2, the reason for the poor floatability of sample 1 immediately after mixing is considered to be the time required for forming the structure. However, it was found that the sample becomes a utilizable liquid medium composition over time.

Further, from the results of Table 2, it was found that even when the first liquid had a high concentration and the difference in volume between the two liquids (the difference in flow velocity) increased, it was possible to stably prepare a liquid medium composition which was preferably mixed.

Example 2

In this example, except that methylcellulose (Pure Chemical Co., Ltd.) was added to the first liquid, mixing was performed in the same manner as in Example 1 above, and the floatability and visibility of the resulting medium composition was evaluated in the same manner as in Example 1 above.

As the first liquid, 500 mL of an aqueous solution containing 0.04 wt % of deacylated gellan gum and 0.63 wt % of methylcellulose was prepared.

Table 3 below shows the volume mixture ratio of the first liquid and the second liquid, the DAG concentration (% (W/v)/methylcellulose concentration (MC concentration (% (W/v))) in the first liquid, the concentration of the liquid medium that is the second liquid, the volume mixture ratio of the two liquids, and the flow velocity when the two liquids are mixed. Table 3 shows the first liquid as A and the second liquid as B as in Table 1. The concentration of the second liquid is shown by the multiplication of the concentration, for example, "×2" (2-fold concentration), with the standard concentration as 1-fold.

TABLE 3

|  | volume mixing ratio A:B | first liquid: total volume DAG concentration/ MC concentration | second liquid: total volume concentration | flow rate (mL/min) |
|---|---|---|---|---|
| sample 5 | 1:1 | 500 mL 0.04%/ 0.63% | 500 mL × 2 | A = 50 B = 50 |
| sample 6 | 1:1 | 500 mL 0.04%/ 0.63% | 500 mL × 2 | A = 25 B = 25 |
| sample 7 | 1:1 | 500 mL 0.04%/ 0.63% | 500 mL × 2 | A = 50 B = 50 |
| sample 8 | 1:1 | 500 mL 0.04%/ 0.63% | 500 mL × 2 | A = 25 B = 25 |

The temperature during mixing, floatability after mixing and visibility are shown in the following Table 4.

TABLE 4

|  | temperature during mixing | floatability (immediately after mixing) | floatability (one day later) | visibility (light transmission rate) |
|---|---|---|---|---|
| sample 5 | room temperature | Δ | Δ | 90.8% |
| sample 6 | room temperature | Δ | ○ | 91.1% |
| sample 7 | 37° C. | Δ | ○ | 90.1% |
| sample 8 | 37° C. | ○ | ○ | 91.1% |

From the results of Table 4, it was found that even if methylcellulose was further added to the first liquid, a liquid medium composition preferably mixed can be prepared.

In the following Examples 3 to 5, the same production apparatus as in Example 1 was used, and the same first and second liquids were used, and mixing was performed by changing the volume mixing ratio and the flow rate of the first and second liquids to various values, which are important among factors affecting the floatability of the culture medium, to confirm the floatability and visibility of the liquid culture medium composition obtained as a result.

The floatability was evaluated using polystyrene beads having diameters of 600 micrometers and manufactured by Polysciences Corporation in the same manner as in Example 1.

For visibility, it was visually determined whether the structure formed by mixing the two liquids was uniformly dispersed in the culture medium composition. Hereinafter, the structures that gathered locally in the medium composition and became visually confirmable is referred to as a "gel-like body".

The concentration of the second liquid is shown by the multiplication of the concentration, for example, "2-fold" concentration, with the standard concentration as 1-fold.

In the following Examples 3 to 5, the time required to obtain 100 mL of the liquid medium composition to be produced is referred to as the "yield time".

Example 3

In this example, the mixed state in the case where the flow velocity was changed was examined with respect to the volume mixing ratio of 1:1, which is considered to be the most easily preferable mixed state.

The mixing was performed by changing the flow rates of the two liquids to 50 mL/min (Run 1), 1 mL/min (Run 2), and 0.1 mL/min (Run 3) while maintaining the volume mixing ratio of the first liquid to the second liquid to be 1:1 (i.e., the flow rates of the first liquid and the second liquid to be the same as each other). The floatability and visibility of the mixed liquid medium composition are shown in Table 5 below.

TABLE 5

| Run | A first liquid DAG concentration (%) | B second liquid concentration (times) | volume mixing ratio A:B | flow rate of A, B A/B (mL/min) | temperature (° C.) | recovery time (sec) | floatability | visibility (presence or absence of gel-like body) |
|---|---|---|---|---|---|---|---|---|
| 1 | 0.03 | 2 | 1:1 | 50/50 | 22.6 | 60 | ○ | none |
| 2 |  |  |  | 1/1 |  | 3000 | ○ | none |
| 3 |  |  |  | 0.1/0.1 |  | 12000 | ○ | none |

As shown in Table 5 above, when the volume mixing ratio of the first liquid to the second liquid was fixed to 1:1, even if the flow rates of the two liquids were changed to 50 mL, 1 mL, and 0.1 mL/min, the gel-like body was not confirmed, and the deterioration of the floatability of the beads was not confirmed. In Runs 1 to 3, although the beads settled slightly immediately after mixing, they became well dispersed after inversion mixing after 24 hours had elapsed.

Example 4

In this example, the mixed state in the case where the flow rate was changed was examined with respect to the volume mixing ratio (first liquid:second liquid)=(1:19)) at which the gel-like body was considered to be relatively likely to occur.

Figure 7:
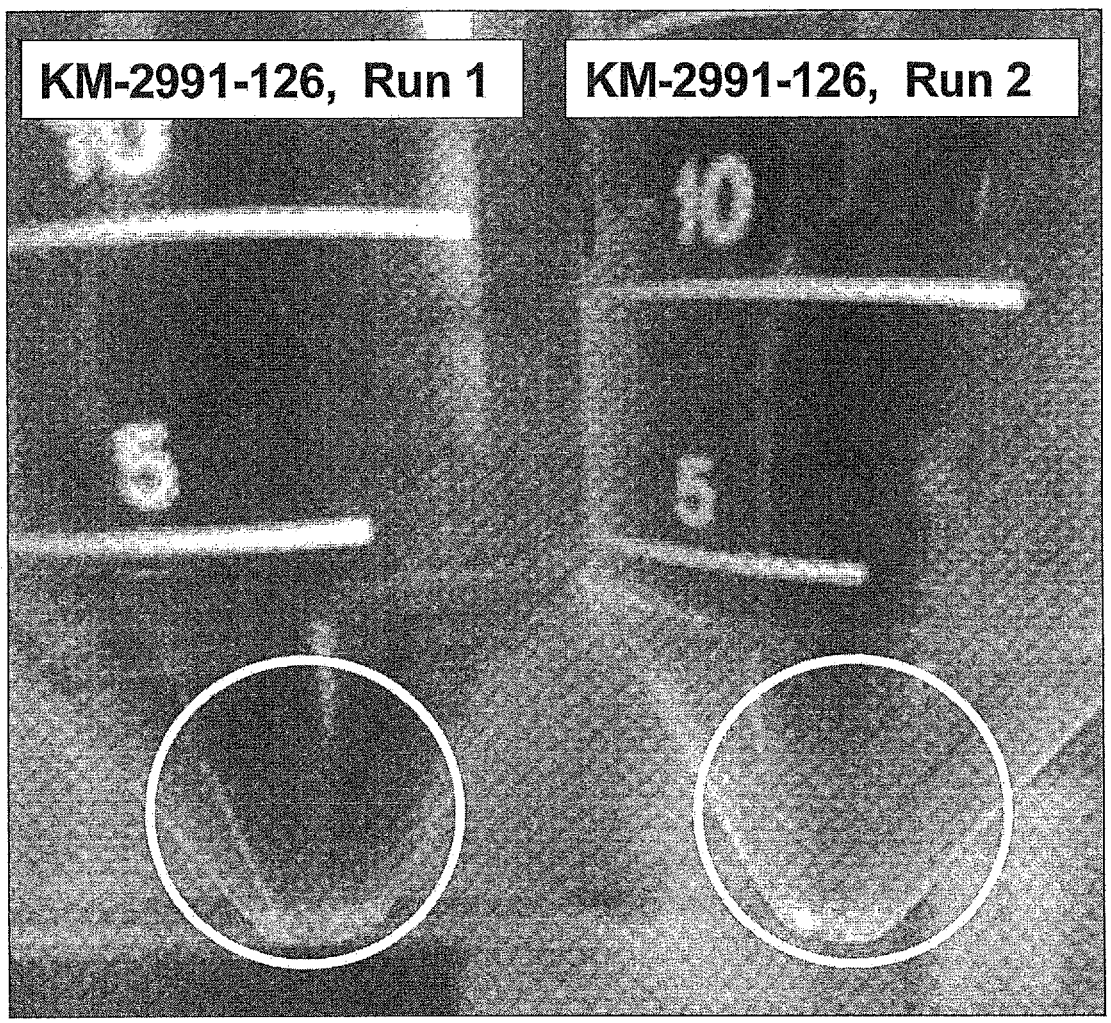
FIG. 7 is a photograph showing the dispersion state of beads in the bottom part (enclosed with white circle) of the conical tube in Run 1 and Run 2 in Example 4 of the present invention.

The flow rates (mL/min) of the two liquids were changed to 2.6/50 (Run 1), 0.1/1.9 (Run 2), 0.4/7.6 (Run 3), 0.8/15.2 (Run 4), 0.5/9.5 (Run 5), 0.6/11.4 (Run 6), and 0.7/13.3 (Run 7) so that the volume mixing ratio of the first liquid and the second liquid were kept at 1:19. The floatability and visibility of the mixed liquid medium composition are shown in Table 6 below. In addition, the state of dispersing the beads at the bottom of the conical tube in the Run 1 and the Run 2 is shown in the photograph of FIG. 7.

As shown in Table 7 above, the beads tended to settle at the volume mixing ratio of Runs 1 to 3, and it was found that the beads floated at the volume mixing ratio of Runs 4 and 5. From the results of this example, it was clarified that the boundary between the sedimentation and the floating of the beads is between the volume mixing ratio of 1:4 and 1:3 when the total flow rate is 2.0 mL/min.

TABLE 6

| Run | A first liquid DAG concentration (%) | B second liquid concentration (times) | volume mixing ratio A:B | flow rate of A, B A/B (mL/min) | temperature (° C.) | recovery time (sec) | floatability | visibility (presence or absence of gel-like body) |
|---|---|---|---|---|---|---|---|---|
| 1 | 0.3 | 1.0 | 1:19 | 2.6/50 | 22.0 | 120 | ○ | none |
| 2 | | | | 0.1/1.9 | | 3000 | Δ | a little opaque |
| 3 | | | | 0.4/7.6 | | 750 | Δ | a little opaque |
| 4 | | | | 0.8/15.2 | | 375 | ○ | a little opaque |
| 5 | | | | 0.5/9.5 | | 600 | Δ | a little opaque |
| 6 | | | | 0.6/11.4 | | 500 | Δ | a little opaque |
| 7 | | | | 0.7/13.3 | | 430 | ○ | a little opaque |

As shown in Table 6 above, when the volume mixing ratio of the first liquid and the second liquid was fixed at 1:19, the gel-like body was not confirmed in all the conditions, but the whole liquid medium was slightly opaque in the Run 2-Run 3. The floatability was evaluated as "A" in the Run 2, the Run 3, the Run 5, and the Run 6, and the beads tended to settle downward from the liquid surface as a whole. In Run 2 and Run 3, the beads tended to settle more than Run 5 and Run 6. Run 2 showed a tendency to settle more than Run 3.

Example 5

Figure 8:
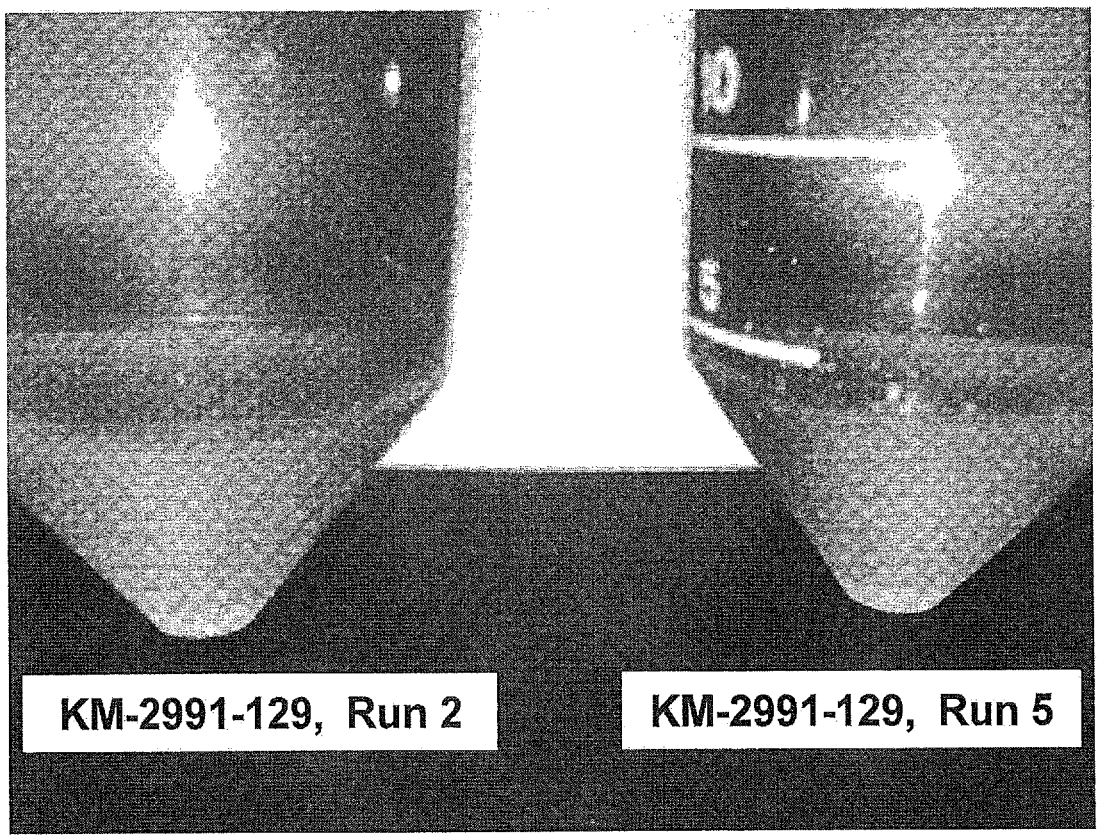
FIG. 8 is a photograph showing the dispersion state of beads in the bottom part of the conical tube in Run 1 and Run 2 in Example 5 of the present invention.

In this example, the total flow rate of the first liquid and the second liquid to be mixed was fixed at 2.0 mL/min, and the mixed state was examined when the volume mixing ratio was changed from 1:2 to 1:9. In the mixing of the two liquids according to the present invention, it is considered that as the ratio of DAG to the total flow rate is lowered and the ratio of the liquid medium is raised, the floatability of the mixed liquid medium composition is deteriorated, and therefore, in this example, the boundary between the sedimentation and the floatation of the beads was examined. The floatability and visibility of the mixed liquid medium composition are shown in Table 7 below. In addition, the state of dispersing the beads at the bottom of the conical tube in Run 2 and Run 5 is shown in the photograph of FIG. 8.

As is clear from Examples 3 to 5 above, no obvious gel-like substance was observed under all conditions. On the other hand, when the volume mixing ratio was fixed at 1:19, deterioration of the floatability of the beads (evaluation Δ) was confirmed in the range of the flow rate of 0.1/1.9 to 0.6/11.4 (mL/min), and when the total flow rate was fixed at 2.0 mL/min, it was found that there was a boundary of quality of the floatability of the beads (evaluation Δ and evaluation ○) between the volume mixing ratio of 1:4 and 1:3.

INDUSTRIAL APPLICABILITY

The production method and the production apparatus of the present invention allow a liquid containing a particular compound to be aseptically, easily and preferably mixed with any liquid containing a linking substance such as a divalent metal cation. As a result, a liquid medium composition in which a fine structure is dispersed can be obtained inexpensively and in a large amount.

This application is based on a patent application No. 2016-144953 (filing date: Jul. 22, 2016), the contents of which are incorporated in full herein.

TABLE 7

| Run | A: first liquid DAG concentration (%) | B second liquid concentration (times) | volume mixing ratio A:B | flow rate of A, B A/B (mL/min) | temperature (° C.) | recovery time (sec) | floatability | visibility (presence or absence of gel-like body) |
|---|---|---|---|---|---|---|---|---|
| 1 | 0.09 | 1.17 | 1:5 | 0.3/1.7 | 20.1 | 1500 | Δ | a little opaque |
| 2 | 0.15 | 1.10 | 1:9 | 0.2/1.8 | | 1500 | Δ | a little opaque |
| 3 | 0.075 | 1.2 | 1:4 | 0.4/1.6 | 20.6 | 1500 | Δ | a little opaque |
| 4 | 0.06 | 1.25 | 1:3 | 0.5/1.5 | | 1500 | ○ | none |
| 5 | 0.045 | 1.33 | 1:2 | 0.7/1.3 | | 1500 | ○ | none |

EXPLANATION OF SYMBOLS 1 first liquid
2 second liquid
3 mixture (liquid medium composition)
10 junction conduit structure
11 first inlet conduit
12 second inlet conduit
13 outlet conduit
S1 first liquid supply source
S2 second liquid supply source
C1 connecting pipe
C2 connecting pipe
C3 supplying pipe

The invention claimed is:

1. A method for producing a liquid medium composition, comprising
   using a junction conduit structure consisting of a first inlet conduit and a second inlet conduit joined together to form an outlet conduit, and
   flowing a first liquid containing a particular compound of the following (i) into the first inflow conduit and flowing a second liquid containing a linking substance of the following (ii) into the second inlet conduit, and allowing the flows of the first and second liquids to join together to sterilely mix the first and second liquids in a closed system configuration without allowing the first and second liquids to contact the outside air,
   thus forming the liquid medium composition comprising structures formed by the particular compound linked via the linking substance dispersed therein while being flown through the outlet conduit:
   (i) a particular compound which is a polymer compound having an anionic functional group, and capable of forming a structure by linking via a divalent metal cation, which structure being capable of suspending a cell or a tissue,
   (ii) a linking substance which is a divalent metal cation,
   wherein the first liquid has a flow velocity of 0.5 m/min to 250 m/min, and the second liquid has a flow velocity of 0.5 m/min to 250 m/min.

2. The method for producing a liquid medium composition according to claim 1, wherein
   the particular compound of (i) is deacylated gellan gum, the first liquid is an aqueous solution containing deacylated gellan gum,
   the linking substance of (ii) is one or both of calcium ion and magnesium ion, and the second liquid is a liquid culture medium containing one or both of calcium ion and magnesium ion or a concentrated liquid of the liquid culture medium.

3. The method for producing a medium composition according to claim 2, wherein a concentration of the deacylated gellan gum in the liquid medium composition is 0.001% (w/v) to 1.0% (w/v).

4. The method for producing a medium composition according to claim 1, wherein, in the junction conduit structure,
   (a) the first inlet conduit and the second inlet conduit are aligned in a straight line such that the first liquid and the second liquid collide with each other facing opposite directions, and the outlet conduit extends forming a right angle to the first inlet conduit and the second inlet conduit, or
   (b) the first inlet conduit and the second inlet conduit are aligned in a V-shape such that the first liquid and the second liquid collide with each other forming a V-shape, and the outlet conduit extends from the confluence part in a direction dividing the internal angle of the V-shape into two equal portions.

* * * * *